US008296101B1

(12) United States Patent
Barlow et al.

(10) Patent No.: US 8,296,101 B1
(45) Date of Patent: Oct. 23, 2012

(54) SYSTEMS AND METHODS FOR EVALUATING ENVIRONMENTAL ASPECTS OF SHIPPING SYSTEMS

(75) Inventors: Arnold Barlow, Atlanta, GA (US);
Dennis R. Estep, Duluth, GA (US);
Andrew J. Gruber, Chicago, IL (US);
Patrick McDavid, Warrenville, IL (US);
Quinto Marini, Plainfield, IL (US);
Nancy Parmer, Roswell, GA (US)

(73) Assignee: United Parcel Service of America, Inc., Atlanta, GA (US)

( * ) Notice: Subject to any disclaimer, the term of this patent is extended or adjusted under 35 U.S.C. 154(b) by 306 days.

(21) Appl. No.: 12/704,800

(22) Filed: Feb. 12, 2010

Related U.S. Application Data

(60) Provisional application No. 61/152,037, filed on Feb. 12, 2009.

(51) Int. Cl.
*G06F 11/30* (2006.01)
*G06F 19/00* (2011.01)
*B65B 1/00* (2006.01)

(52) U.S. Cl. .................. 702/182; 700/115; 53/503

(58) Field of Classification Search .................. 702/182; 707/812; 700/115; 705/10; 53/503
See application file for complete search history.

(56) References Cited

U.S. PATENT DOCUMENTS

| | | | |
|---|---|---|---|
| 6,877,297 B2 * | 4/2005 | Armington et al. ............ 53/502 |
| 7,813,970 B1 | 10/2010 | Brandwine et al. | |
| 2005/0021389 A1 | 1/2005 | Dias et al. | |
| 2005/0154669 A1 | 7/2005 | Streetman | |
| 2006/0089851 A1 | 4/2006 | Silby et al. | |
| 2007/0255457 A1 | 11/2007 | Whitcomb et al. | |
| 2008/0040182 A1 | 2/2008 | Wegner et al. | |
| 2009/0055232 A1 | 2/2009 | Bruno et al. | |
| 2009/0187493 A1 | 7/2009 | Whiteman | |
| 2009/0210295 A1 | 8/2009 | Edholm et al. | |

FOREIGN PATENT DOCUMENTS

EP  1887499  2/2008

OTHER PUBLICATIONS

"uShip Makes Shipping Greener Easy," Uship Press Release dated Jan. 16, 2007, 2 pages, http://www.uship.com/read_article.aspx?uID=1051&PID=1043.

"Carbonfund.org Pioneers Carbonfree Shipping," Carbonfund.org Press Release dated Nov. 16, 2006; 2 pages, http://www.carbonfund.org/site/more/media/255.

"Ista 3A Standard: Packaged-Products for Parcel Delivery System Shipment 70 kg (150 lb) or Less," Ista 3 Series General Simulation Performance Test Procedure, last editorial change dated Jan. 2009, 28 pages, http://www.ista.org/forms/3Aoverview.pdf.

* cited by examiner

*Primary Examiner* — Bryan Bui
(74) *Attorney, Agent, or Firm* — Alston & Bird LLP

(57) ABSTRACT

According to various embodiments, package evaluation systems and methods are provided for evaluating the sustainability of packaging used in the shipment of goods. In particular, the package evaluation systems and methods are configured for performing package evaluations and managing and providing access to data resulting from package evaluations. The package evaluations are designed to assess, among other things, the ability of sample packages to prevent damage to their contents, the volumetric efficiency of sample packages, and the sustainability of the materials used to construct sample packages. In addition, the systems and methods are further configured for assigning a certification to an entity associated with the evaluated packages based on the results of the evaluation.

41 Claims, 23 Drawing Sheets

SHIPPER INFORMATION FORM

| | |
|---|---|
| Customer Name: | |
| Primary shipper number: | |
| Secondary shipper numbers: | |
| Total annual small parcel shipments : | |
| Number of different box types shipped: | |
| Do you ship liquid products? | Yes / No |
| | *If yes, indicate using "(liquid.)" in the product description* |
| Do you ship stringed instruments? | Yes / No |
| | *If yes, indicate using "(S.I.)" in the product description* |
| Do you ship products in fiber wound tubes? | Yes / No |
| | *If yes, indicate using "(tube)" in the product description* |
| Do you ship temperature sensitive products? | Yes / No |
| | *If yes, indicate using "(temp.)" in the product description* |
| Does your WMS provide information on product and carton sizes for individual shipments? | Yes / No |

FIGURE 6

DAMAGE PREVENTION PACKAGE INFORMATION FORM

| Box Type A1 | |
|---|---|
| Description of product(s): | |
| What constitutes damage to the product(s)? | |
| What damage tolerance level is allowable, if any? | |
| What is an acceptable condition of the package at conclusion of testing? | |
| Heaviest configuration: | |
| Most fragile configuration: | |

| Box Type (N) | |
|---|---|
| Description of product(s): | |
| What constitutes damage to the product(s)? | |
| What damage tolerance level is allowable, if any? | |
| What is an acceptable condition of the package at conclusion of testing? | |
| Heaviest configuration: | |
| Most fragile configuration: | |

FIGURE 7

PRODUCT-PACKAGE DIMENSION INFORMATION FORM

| Box Type ID | Product Type ID | Fragility Class | Packing Configuration | Box Dimensions (inches) | | | Product Dimensions (inches) | | |
|---|---|---|---|---|---|---|---|---|---|
| | | | | Length | Width/ Diameter | Height / Thickness | Length | Width | Height |
| | | | | | | | | | |
| | | | | | | | | | |
| | | | | | | | | | |

PACKAGE MATERIAL INFORMATION FORM

| Packaging Material 1 | | |
|---|---|---|
| | | Verification By/Date/Comments |
| Material Type | | |
| Locations of Utilization (Shipper Numbers) | | |
| Supplier & Supplier Address | | |
| Reusability | Is material reused? If yes, how many trips? Please provide proof of actual reuse practices. | |
| Recycled Content | Please provide any recycled content information provided by supplier. | |
| Packaging Material (N) | | |
| | | Verification By/Date/Comments |
| Material Type | | |
| Locations of Utilization (Shipper Numbers) | | |
| Supplier & Supplier Address | If <100 miles from location of utilization, please provide documentation. | |
| Reusability | Is material reused? If yes, how many trips? Please provide proof of actual reuse practices. | |
| Recycled Content | Please provide any recycled content information provided by supplier. | |

FIGURE 9

| Shipper Certification Profile – Certification Level | | | | | |
|---|---|---|---|---|---|
| Shipper: | ABC Company | | | | |
| Primary Shipper Number: | 867 | | | | |
| Final Evaluation Date: | pending | | | | |
| | Damage Prevention Evaluation | Volume Efficiency Evaluation | Package Materials Evaluation | Overall | |
| Score | - | - | - | - | |
| Pass / Fail / Pending | pending | pending | pending | pending | |

FIGURE 10A

| Shipper Certification Profile – Certification Level | | | | | |
|---|---|---|---|---|---|
| Shipper: | ABC Company | | | | |
| Primary Shipper Number: | 867 | | | | |
| Final Evaluation Date: | 01/20/2010 | | | | |
| | Damage Prevention Evaluation | Volume Efficiency Evaluation | Package Materials Evaluation | Overall | |
| Score | - | 83% | - | - | |
| Pass / Fail | Fail | Pass | Pass | Fail | |

| | |
|---|---|
| PACKAGE LABORATORY REPORT | |
| Shipper / PSN: | ABC Company |
| Primary Shipper Number: | 867 |
| Box Type: | A2 – Medium Standard Box |
| Product: | 42 – Six Candles (200 Burn Hours) (most fragile package configuration) |
| Test: | ISTA Test Procedure 3A - Standard |
| Result: | The packaged product has failed to meet the requirements of the ISTA 3A based on the acceptance criteria as outlined in this report. |

*Acceptance Criteria*

No Visible Damage
Product Intact
Packaging components able to provide further protection

*Observations*

1) The corrugated partition showed a significant amount of fatigue. This fatigue allowed the product to shift in the shipping container, and to come into contact with the walls of the shipper. This movement and contact can lead to product damage.

2) Two of the candles had dents on the bottom edges. The damage was most likely caused by the breakdown of the shipping container and partition. This allowed the shocks incurred during testing to be absorbed directly by the product.

*Recommendations*

1) The package failed due to the insufficient strength of the corrugated board. Due to the density and weight of the product, use a stronger corrugated board to construct the shipping container. Consider using a corrugated shipping container constructed from C-flute board with a minimum bursting strength value of 200 pounds per square inch (PSI) and combined weight of facings of 84 pounds per 1000 square feet. This will reduce the risk of break down of the corrugated board.

2) In order to reduce the risk of damage to the product, the strength of the corrugated partitions must be increased. This can be done in two ways: 1) Change the direction of the flutes so that they run in a horizontal orientation; or 2) Increase the Mullen Burst test strength of the partition to 275 pounds per square inch. Either of these options will increase the effectiveness of the partition, and in turn reduce the risk of damage.

FIGURE 12

Shipper Certification Profile – Damage Prevention Evaluation Level

| Shipper / PSN: | ABC Company | | |
|---|---|---|---|
| Primary Shipper Number: | 867 | | |
| Evaluation: | Damage Prevention | | |
| Evaluation Status (pass/fail/pending): | Fail | | |
| Package Type | Associated Product | Pass / Fail / Pending | Linked Document |
| A1_03 (Large Standard Box) | 05 (Light Bulbs) | Pass | DP_Report_867_A105.doc |
| A2_15 (Med. Standard Box) | 42 (Six Candles) | Fail | DP_Report_867_A242.doc |
| B1_01 (Large Flat Box) | 09 (Computer Monitor) | Pass | DP_Report_867_B109.doc |
| A3_12 (Small Standard Box) | 70 (Computer Paper) | Pass | DP_Report_867_A370.doc |
| A3_09 (Small Standard Box) | 78 (Single T-Shirt) | Pass | DP_Report_867_A378.doc |

FIGURE 13

| Fragility Class | Standard Pack Configuration | Pick & Pack Configuration |
|---|---|---|
| Rugged | 80% | 60% |
| Semi-Rugged | 65% | 50% |
| Semi-Delicate | 55% | 45% |
| Delicate | 50% | 40% |
| Fragile | 45% | 35% |

FIGURE 15A

| TUBULAR PACKAGE CHART | | |
|---|---|---|
| Tube Length (ft.) | Minimum Tube Diameter (in.) | Minimum Tube Thickness (in.) |
| 4 | 2 | 3/16 |
| 5 | 3 | 3/16 |
| 6 | 3 | 3/16 |
| 7 | 5 | 3/16 |
| 8 | 5 | 4/16 |
| 9 | 6 | 4/16 |

Shipper Certification Profile – Volume Efficiency Evaluation Level

| Shipper / PSN: | ABC Company |
|---|---|
| Primary Shipper No.: | 867 |
| Evaluation: | Volume Efficiency |
| Evaluation Status (pass/fail/pending): | Pass |
| Average Threshold: | 53.8% |
| Average Product to Package Ratio: | 83.0 % |

SPECIFIC DATA FROM VOLUME EFFICIENCY EVALUATION

| Box Type | Associated Product | Packing Configuration | Fragility Class | Prod. to Pack. Ratio |
|---|---|---|---|---|
| A1 (Large Standard Box) | 05 (Light Bulbs) | Standard Pack | Fragile | 70% |
| A2 (Med. Standard Box) | 42 (Six Candles) | Standard Pack | Semi-Delicate | 85% |
| B1 (Large Flat Box) | 09 (Computer Monitor) | Pick & Pack | Delicate | 81% |
| A3 (Small Standard Box) | 70 (Computer Paper) | Standard Pack | Semi-Rugged | 89% |
| A3 (Small Standard Box) | 78 (Single T-Shirt) | Pick & Pack | Rugged | 90% |

FIGURE 16

| | Shipping Container | | Internal Materials | | | |
|---|---|---|---|---|---|---|
| | Cont. 1 | Cont. 2 | Fill 1 | Fill 2 | Divider 1 | Wrap 1 |
| Material ID | 34 | | 2 | | 34 | 28 |
| Material Type | Paper | | Paper | | Paper | HDPE |
| Conversion: | Corrug. | | Med W K | | Corrug. | Film |
| Basis Weight (lbs. per 1000 ft$^2$) | 80 | | 80 | | 79 | n/a |
| Plastic Thickness (mil) | n/a | | n/a | | n/a | 4 |
| Foam Thickness (in.) | n/a | | n/a | | n/a | n/a |
| Foam Density (PCF) | n/a | | n/a | | n/a | n/a |

Package Materials Calculator User Interface

| | Shipping Container | | | | Internal Materials | | | | | |
|---|---|---|---|---|---|---|---|---|---|---|
| | Yes | No | Yes | No | Yes | No | Yes | No | Yes | No |
| Source Location: Local (within 100 miles) | x | | | | x | | | x | x | |
| Biodegrable: Composting Facility | x | | | | x | | x | | | x |
| Biodegrable: Backyard | x | | | | x | | x | | | x |
| Recyclability: Limited Recycling Available | x | | | | x | | x | | x | |
| Reusability: Average Number of Reuses | 1.0 | | | | 1.0 | | 1.0 | | 1.0 | |
| Material Makeup: Renewable Resource or 50-100 % Recycled Content | x | | | | x | | x | | | x |
| Fossil Fuel Consumption (MJ) | 1.0 | | | | 0.7 | | 0.9 | | 0.0 | |
| GHG Emission (kg CO2) | 1.0 | | | | 0.2 | | 0.9 | | 0.3 | |
| Water Consumption (l) | 0.7 | | | | 0.1 | | 0.7 | | 0.0 | |
| Biotic Resource Consumption (m3) | 0.1 | | | | 0.0 | | 0.1 | | 0.0 | |
| Aquatic Toxicity (CTUe) | 0.2 | | | | 0.0 | | 0.2 | | 0.0 | |
| Mineral Consumption (kg) | 0.3 | | | | 0.0 | | 0.3 | | 0.1 | |
| Eutrophication (kg PO4) | 1.0 | | | | 0.2 | | 0.9 | | 0.1 | |
| Total | 10.3 | | | | 7.2 | | 9 | | 3.5 | |
| Material Weight | 3.2 | | | | 2.5 | | 1.5 | | 0.15 | |
| Internal Material Weight % | 100% | | | | 60% | | 36% | | 4% | |
| Adjusted Total | 10.3 | | | | 4.3 | | 3.2 | | 0.1 | |

| Shipping Container Score | 10.3 |
|---|---|
| Internal Materials Store | 7.6 |
| OVERALL PACKAGE MATERIALS SCORE | 9.0 |

| Shipping Container Strength | |
|---|---|
| Package Weight (lbs) | 12 |
| Box Strength Baseline | 80 |

FIGURE 18

Cushion & Fill Material Lookup Table – Fossil Fuel Consumption

| Material ID | Material Class | Material Type | Relative Fossil Fuel Consumption |
|---|---|---|---|
| 1 | Paper | Tightly Wadded Kraft | 0.6 |
| 2 | Paper | Medium Wadded Kraft | 0.7 |
| 3 | Paper | Loose Wadded Kraft | 0.8 |
| 4 | Paper | Quilted Kraft | 1.0 |
| 5 | Paper | Tightly Wadded Bleached Kraft | 0.3 |
| 6 | Paper | Medium Wadded Bleached Kraft | 0.3 |
| 7 | Paper | Loose Wadded Bleached Kraft | 0.4 |
| 8 | Paper | Shredded Corrugated | 0.6 |
| 9 | Paper | Corrugated | 0.1 |
| 10 | Paper | Molded Pulp | 0.2 |
| 11 | Polystyrene | Fabricated Foam Cushioning | 0.1 |
| 12 | Polystyrene | Loose Fill Foam Peanuts | 0.5 |
| 13 | High-Density Polyethylene | Fabricated Foam Cushioning | 0.2 |
| 14 | High-Density Polyethylene | Large Air Cell | 0.4 |
| 15 | High-Density Polyethylene | Small Air Cell | 0.2 |
| 16 | High-Density Polyethylene | Air Pillow | 0.5 |
| 17 | Low-Density Polyethylene | Fabricated Foam Cushioning | 0.2 |
| 18 | Low-Density Polyethylene | Large Air Cell | 0.4 |
| 19 | Low-Density Polyethylene | Small Air Cell | 0.1 |
| 20 | Low-Density Polyethylene | Air Pillow | 0.5 |
| 21 | Polypropylene | Fabricated Foam Cushioning | 0.2 |
| 22 | Polyurethane | Fabricated Foam Cushioning | 0.2 |
| 23 | Starch | Fabricated Foam Cushioning | 0.3 |
| 24 | Starch | Foam Peanuts | 0.3 |

FIGURE 19

Shipper Certification Profile – Package Materials Evaluation Level

| Shipper / PSN: | ABC Company |
|---|---|
| Primary Shipper Number: | 867 |
| Evaluation: | Package Materials Evaluation |
| Evaluation Status (pass/fail/pending): | Fail |

| Package Type | Associated Product | Shipping Container Score | Internal Materials Score | Overall Package Materials Score | Pass/Fail |
|---|---|---|---|---|---|
| A1_03 (Large Standard Box) | 05 (Light Bulbs) | 11.6 | 5.6 | 8.6 | Fail |
| A2_15 (Med. Standard Box) | 42 (Six Candles) | 10.3 | 7.6 | 9.0 | Pass |
| B1_01 (Large Flat Box) | 70 (Computer Paper) | 13.9 | 8.2 | 11.1 | Pass |
| A3_12 (Small Standard Box) | 78 (Single T-Shirt) | 9.3 | 13.2 | 11.3 | Pass |
| A3_09 (Small Standard Box) | 09 (Computer Monitor) | 12.5 | 10.0 | 11.3 | Pass |
| T1_00 (Large Tube) | 15 (Posters) | 13.8 | 6.9 | 10.4 | Fail |

FIGURE 20

Certification Evaluation Summary

| Customer Information | Shipping Entity Information |
|---|---|
| ABC Company<br>123 S. Main Street<br>Anywhere, GA 30328 | Shipping Entity Package Design and Test lab<br>108 S. Main St.<br>Somewhere, IL 60609<br>404-867-5309 |
| John Q Customer, Sustainability Manager<br>555-333-4343<br>jqcustomer@custo.com | Jane Q. Carrier, Strategic Account Manager<br>202-222-3333<br>jQcarrier@shippingentity.com |
| Customer Number: 867 | |

| Description Of Products, SKUs, or Lines Tested |
|---|
| Textbooks, Candles, Computer Products, and Posters packaged in corrugated cardboard, packages filled with wadded kraft paper. Box types tested are A1, A2, A3, B1, and T1. |

| Criterion | Result | Comments |
|---|---|---|
| Damage Prevention | PASS | Used ISTA 3A |
| Product-to-Package Ratio | PASS | Average 83% |
| Packaging Materials | PASS | Consider molded pulp |
| Final Rating | PASS | Qualified for UPS GreenShipper |

Congratulations on your passing score. If you wish to become a participant in Shipping Entity Sustainability Program, the next steps are:

1. A signed license agreement;
2. Payment of all applicable fees as specified in the license agreement.
*Please note that a signed agreement and payment of all applicable fees (whether initial or renewal) is required before you use the Shipping Entity Sustainability Program logo in any manner or communicate that you are Shipping Entity Sustainability Program qualified. Refer to the License Agreement for all Terms and Conditions.*

FIGURE 22

SYSTEMS AND METHODS FOR EVALUATING ENVIRONMENTAL ASPECTS OF SHIPPING SYSTEMS

CROSS-REFERENCE TO RELATED APPLICATIONS

This application claims priority from provisional U.S. Application No. 61/152,037 entitled "Systems and Methods For Evaluating Environmental Aspects of Shipping Systems," which was filed on Feb. 12, 2009 and is herein incorporated by reference.

BACKGROUND OF THE INVENTION

As awareness of environmental issues has grown, customers of shipping companies have become increasingly concerned with the impact of their shipping activities on the environment. Many shipping customers (e.g., sellers of goods) are interested in evaluating and optimizing the sustainability of their shipping practices. In particular, certain shipping customers are interested in evaluating their transport packaging systems and optimizing the various packaging used as part of their transport packaging systems to ship products. These shipping customers may also be interested in communicating their environmental awareness to the recipients of their packages and enabling those recipients to distinguish sellers using environmentally responsible shipping practices.

Accordingly, there is a need in the art for improved systems and methods for evaluating the sustainability of transport packaging systems and for communicating the sustainability of shipping customers' transport packaging systems (as determined by the evaluation) to recipients of packages from shipping company customers. In addition, there is a need for such a system to provide shipping company customers with an indication of which aspects of their shipping practices may be improved based on the evaluation. Furthermore, there is a need for such a system to provide a level of transparency and accountability in order to ensure confidence by recipients of packages in the legitimacy of the evaluation process.

BRIEF DESCRIPTION OF DRAWINGS

Figure 1:
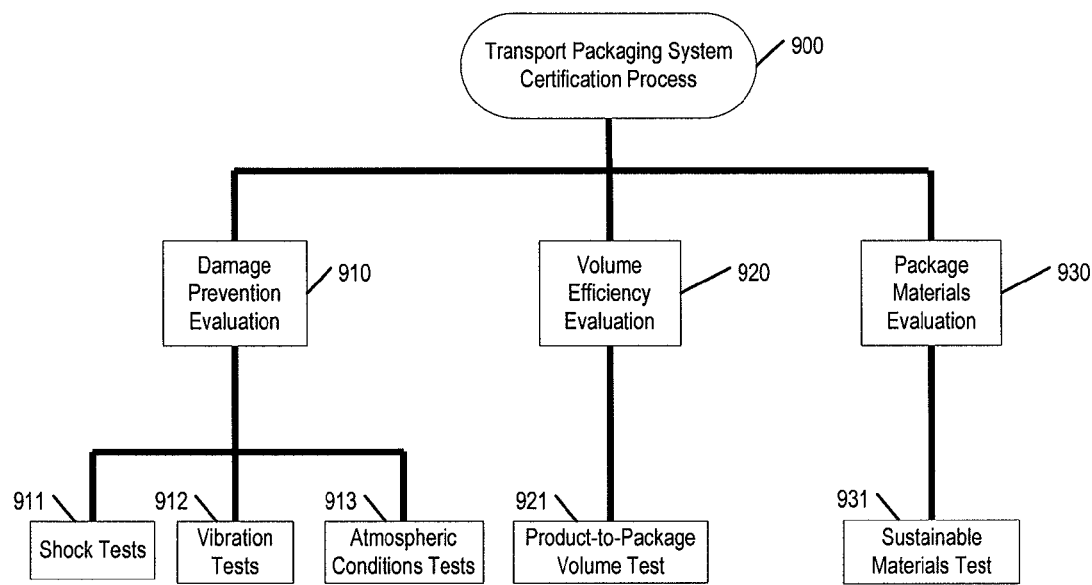

Having thus described the invention in general terms, reference will now be made to the accompanying drawings, which are not necessarily drawn to scale, and wherein:

FIG. 1 is a block diagram of exemplary evaluations and tests comprising a transport packaging system evaluation according to one embodiment of the present invention.

Figure 2:
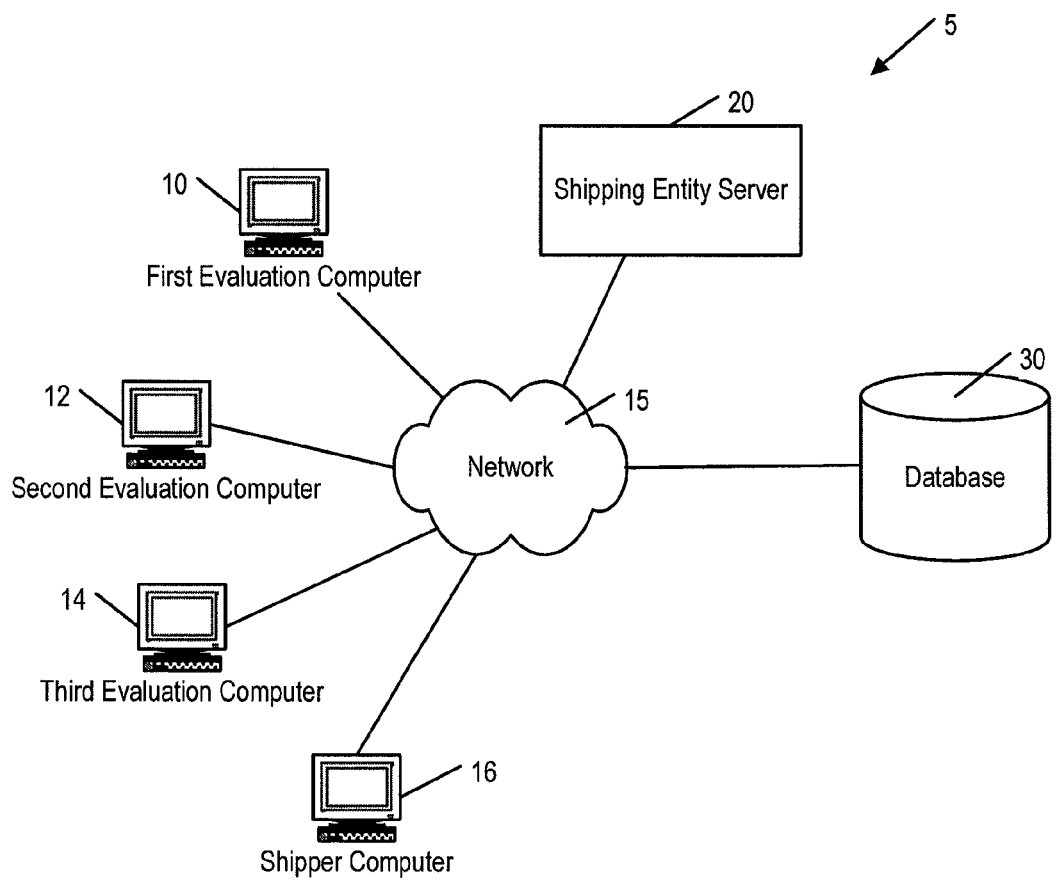

FIG. 2 is a block diagram illustrating a package evaluation system according to one embodiment of the present invention.

Figure 3:
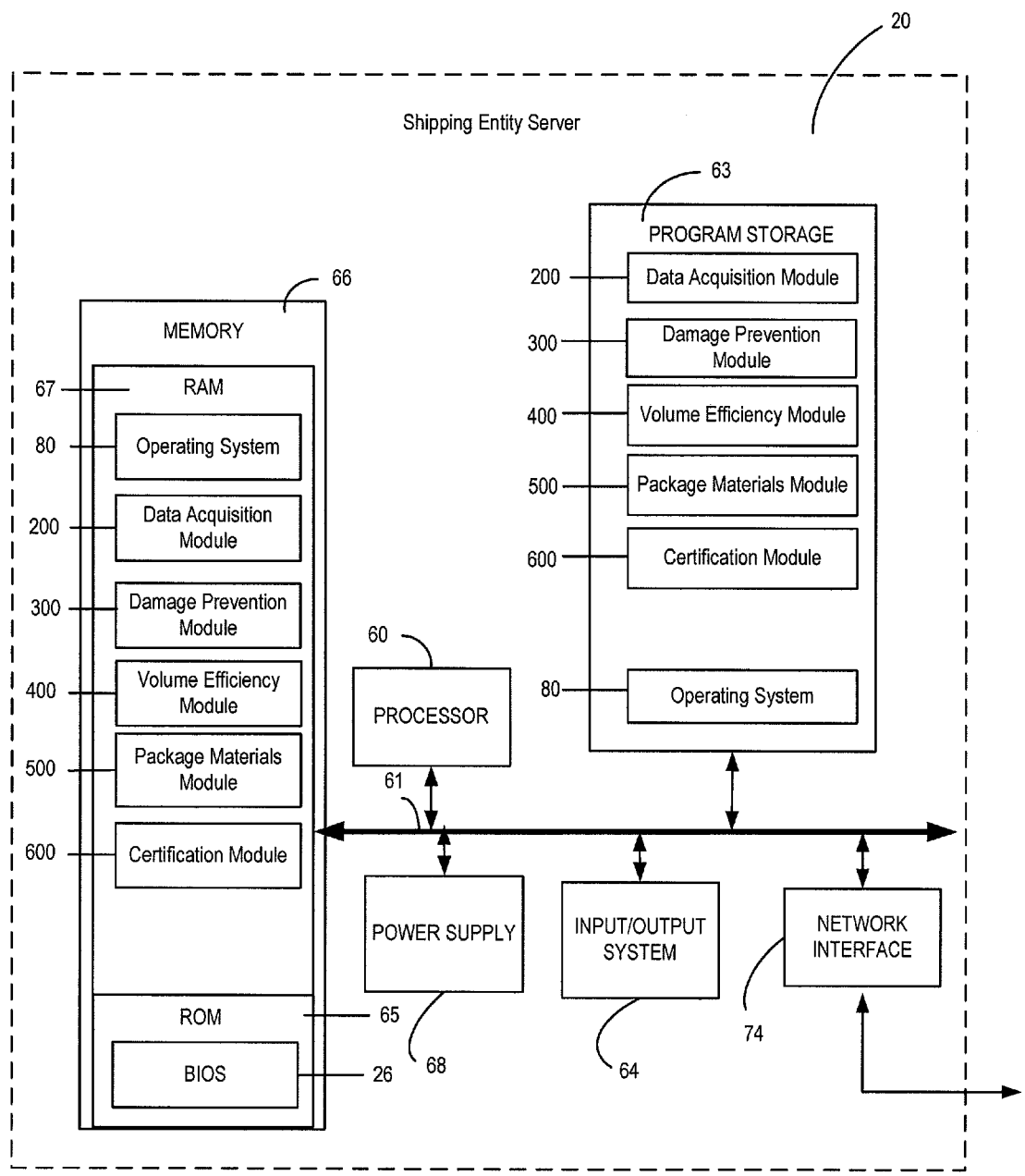

FIG. 3 is a schematic diagram of a shipping entity server according to one embodiment of the present invention.

Figure 4:
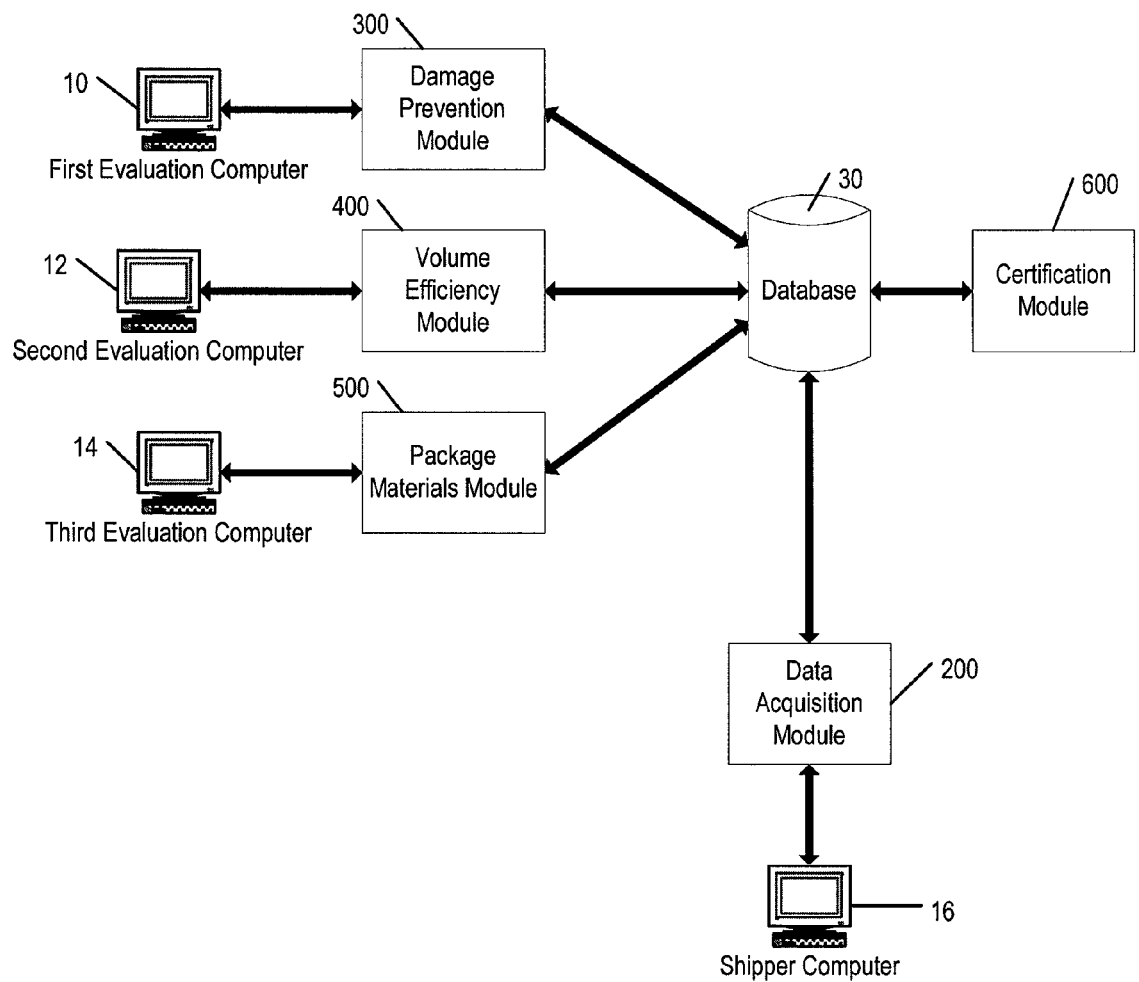

FIG. 4 is a schematic diagram illustrating the interaction of various components of a package evaluation system according to one embodiment of the present invention.

Figure 5:
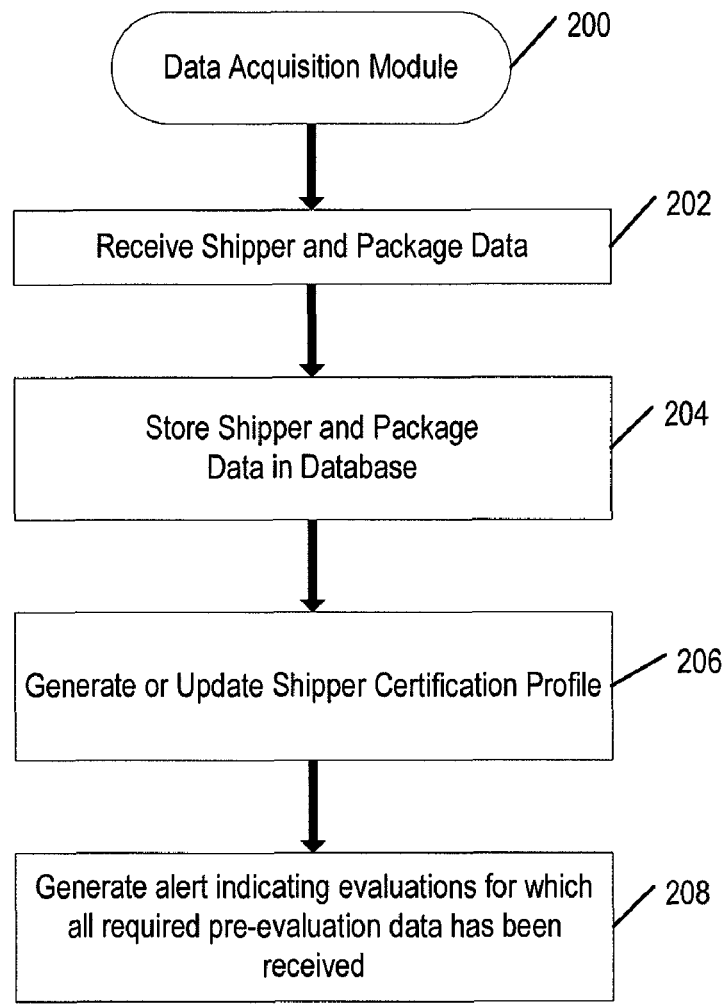

FIG. 5 is a flow diagram illustrating steps executed by the data acquisition module according to one embodiment of the present invention.

FIG. 6 is a block diagram of a shipper information form according to one embodiment of the present invention.

FIG. 7 is a block diagram of a damage prevention package information form according to one embodiment of the present invention.

FIG. 8 is a block diagram of a product-package dimension information form according to one embodiment of the present invention.

FIG. 9 is a block diagram of a package material information form according to one embodiment of the present invention.

FIG. 10A is a block diagram of a new shipper certification profile viewed at the certification level according to one embodiment of the present invention.

FIG. 10B is a block diagram of an updated shipper certification profile viewed at the certification level according to one embodiment of the present invention.

Figure 11:
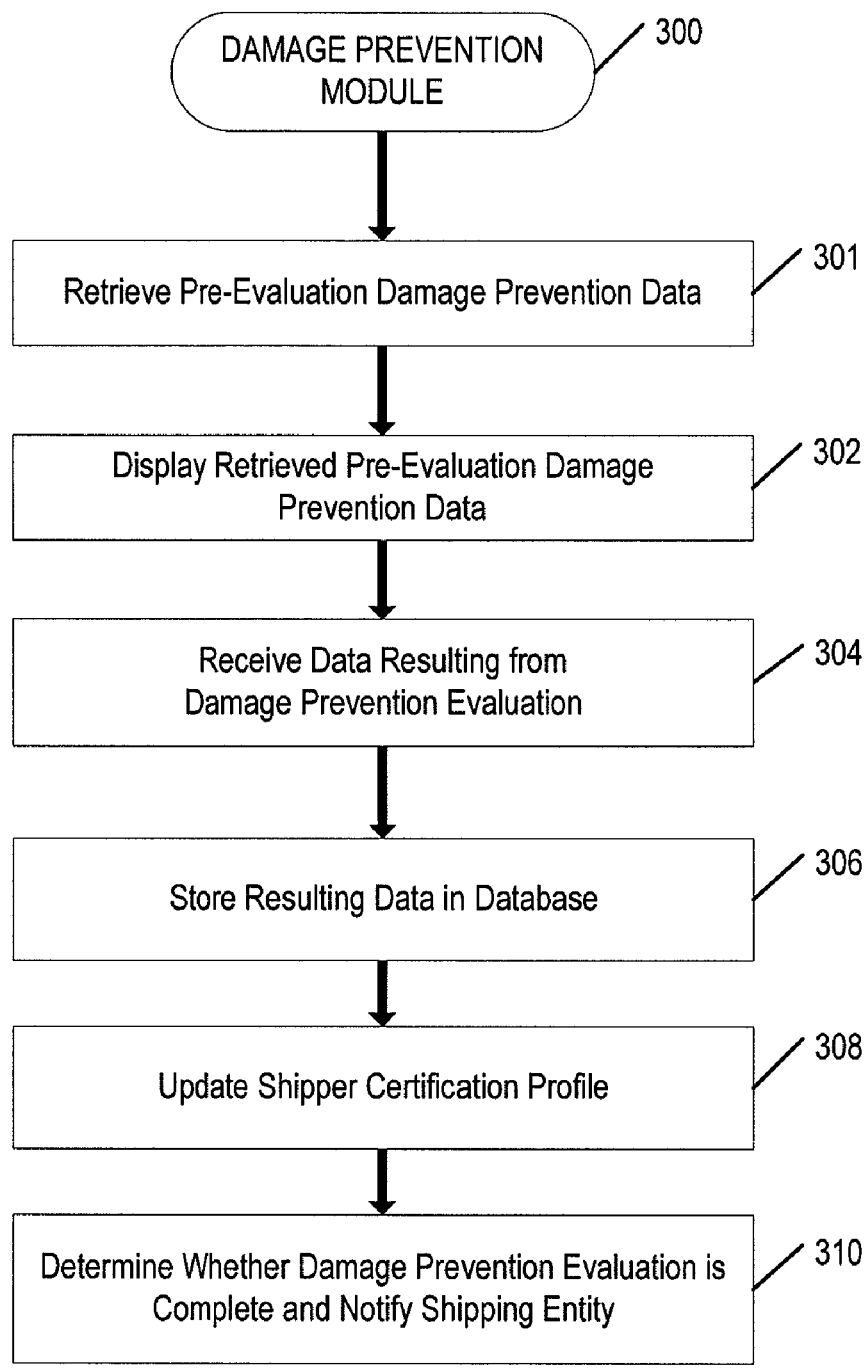

FIG. 11 is a flow diagram of steps executed by the damage prevention module according to one embodiment of the present invention.

FIG. 12 is a block diagram of a package laboratory report according to one embodiment of the present invention.

FIG. 13 is a block diagram of a shipper certification profile viewed at the damage prevention evaluation level according to one embodiment of the present invention.

Figure 14:
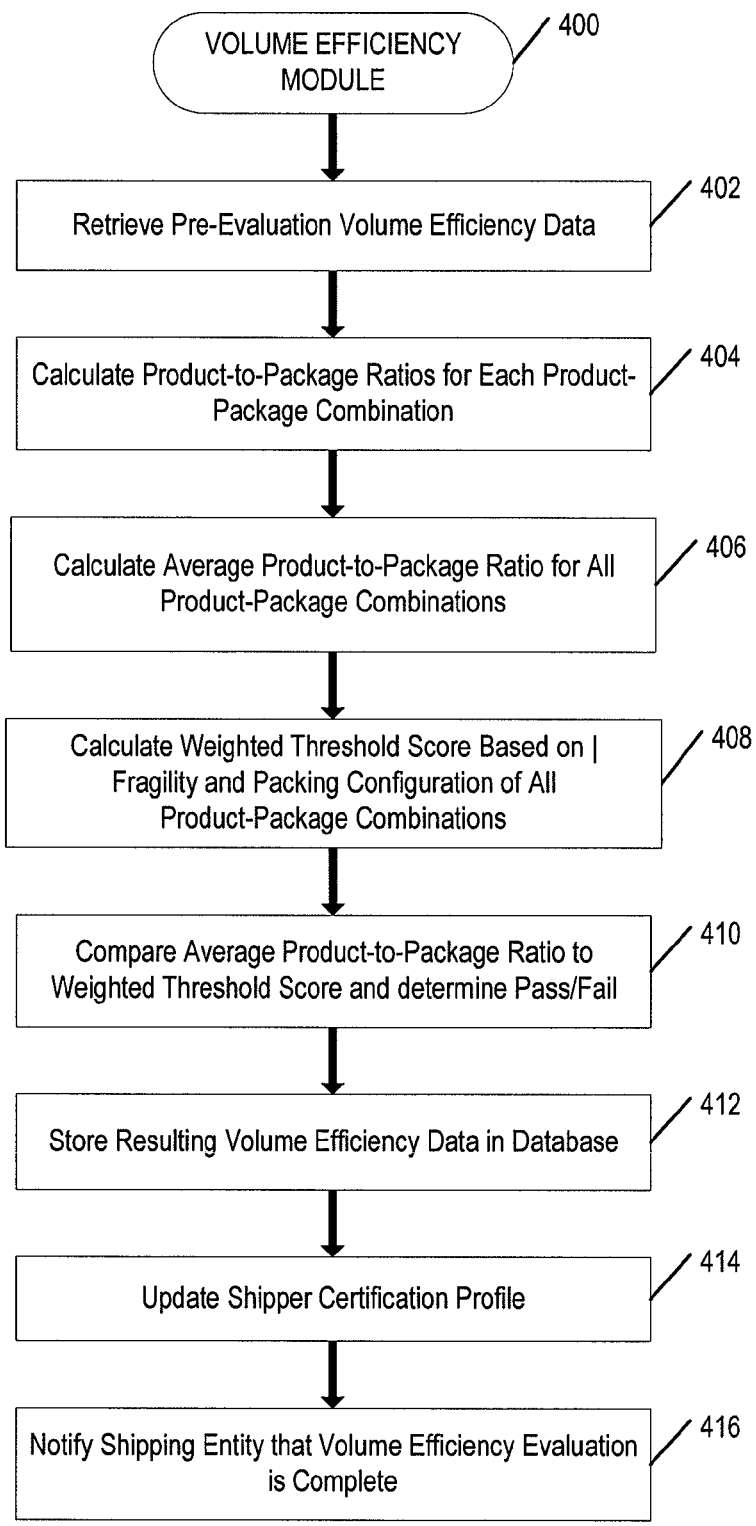

FIG. 14 is a flow diagram of a steps executed by the volume efficiency module according to one embodiment of the present invention.

FIG. 15A is a block diagram of a volume efficiency threshold table according to one embodiment of the present invention.

FIG. 15B is a block diagram of a volume efficiency threshold table for tubular packages according to one embodiment of the present invention.

FIG. 16 is a block diagram of a shipper certification profile viewed at the volume efficiency evaluation level according to one embodiment of the present invention.

Figure 17:
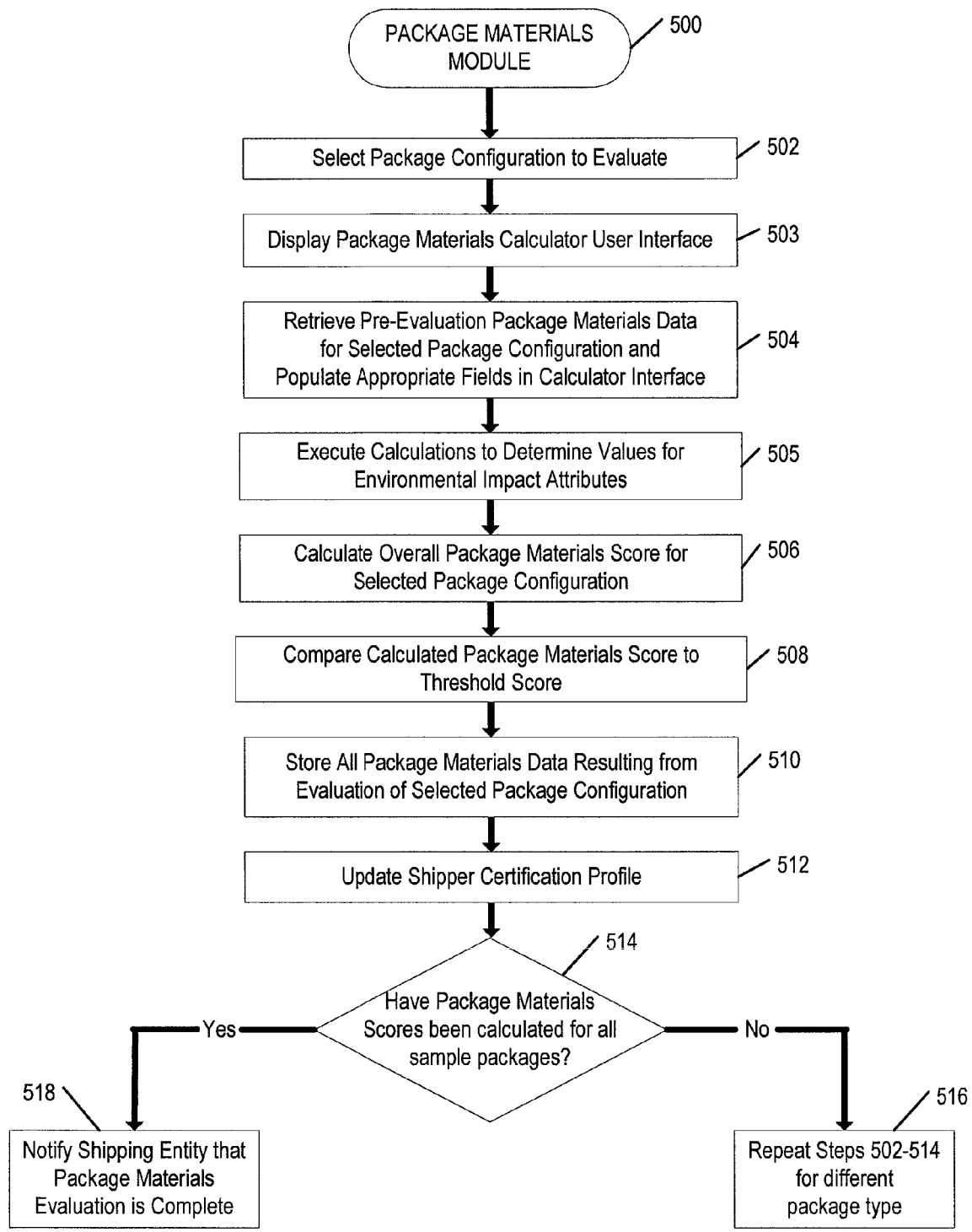

FIG. 17 is a flow diagram of steps executed by the package materials module according to one embodiment of the present invention.

FIG. 18 is a block diagram of the package materials calculator user interface according to one embodiment of the present invention.

FIG. 19 is a block diagram of a cushion and fill material lookup table according to one embodiment of the present invention.

FIG. 20 is a block diagram of a shipper certification profile viewed at the package materials evaluation level according to one embodiment of the present invention.

Figure 21:
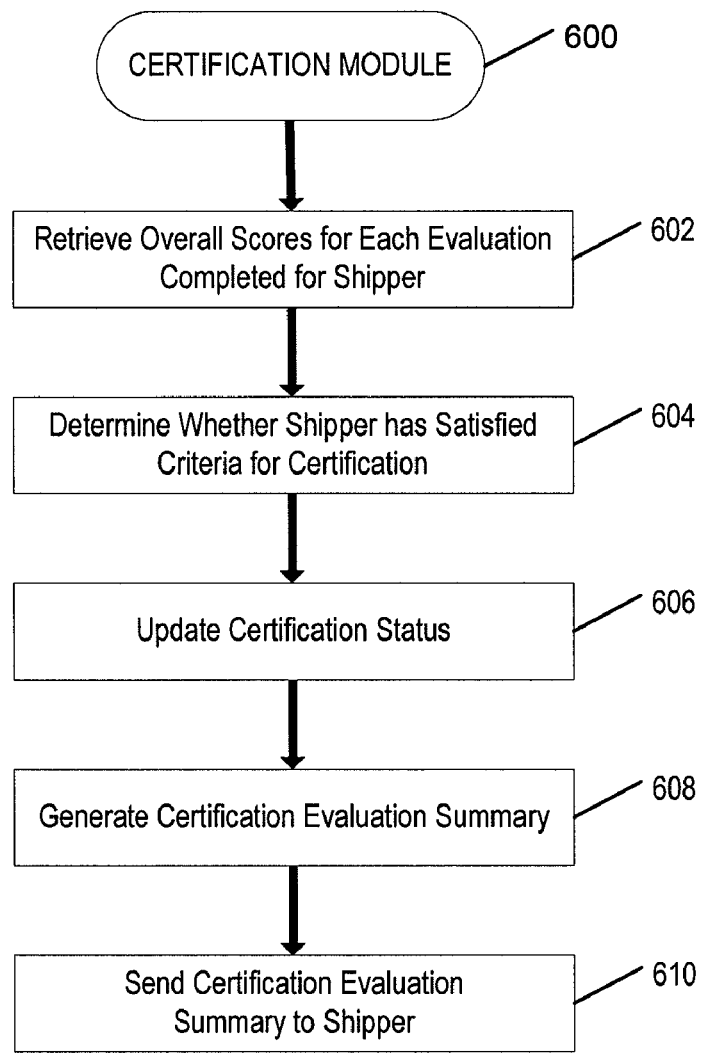

FIG. 21 is a flow diagram of steps executed by the certification module according to one embodiment of the present invention.

FIG. 22 is a block diagram of a certification evaluation summary according to one embodiment of the present invention.

Figure 23:
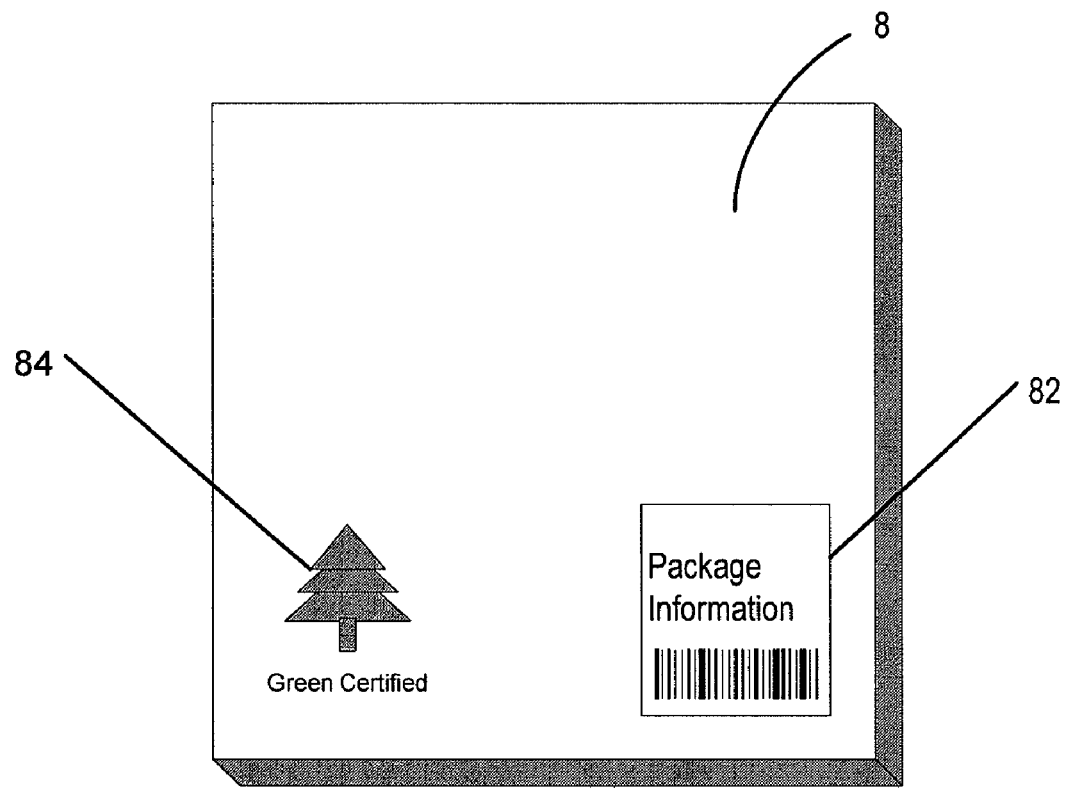

FIG. 23 is a schematic diagram illustrating a package having a certification logo and package information printed thereon according to various embodiments of the present invention.

BRIEF SUMMARY OF THE INVENTION

According to various embodiments, package evaluation systems and methods are provided for evaluating the sustainability of packaging used in the shipment of goods. Various embodiments include a method for evaluating the sustainability of packaging used for shipping goods, the method comprising the steps of receiving, via one or more processors, damage prevention data pertaining to the ability of a first set of one or more packages to prevent damage to a first set of one or more items; storing the damage prevention data in one or more memory storage areas; receiving, via the one or more processors, volume efficiency data, the volume efficiency data pertaining to the relative volume of a second set of one or more packages and a second set of one or more items; storing the volume efficiency data in at least one of the memory storage areas; receiving, via said one or more processors, package materials data pertaining to the sustainability of one or more package materials used to construct a third set of one or more packages; storing the package materials data in at least one of the memory storage areas; determining, via said one or more processors, based on the damage prevention data, the volume efficiency data, and the package materials data, whether the first set of packages, the second set of packages, and the third set of packages have satisfied a set of predefined sustainability criteria.

Various embodiments also include a system for evaluating the sustainability of packaging used for shipping goods, the system comprising: one or more memory storage areas; and one or more processors configured for executing the steps of: receiving damage prevention data pertaining to the ability of a first set of one or more packages to prevent damage to a first set of one or more items; storing the damage prevention data in one or more memory storage areas; receiving volume efficiency data, the volume efficiency data pertaining to the relative volume of a second set of one or more packages and a second set of one or more items; storing the volume efficiency data in at least one of the memory storage areas; receiving package materials data pertaining to the sustainability of one or more package materials used to construct a third set of one or more packages; storing the package materials data in at least one of said memory storage areas; determining based on the damage prevention data, the volume efficiency data, and the package materials data, whether the first set of packages, the second set of packages, and the third set of packages have satisfied a set of predefined sustainability criteria.

Various embodiments also include a system for evaluating the sustainability of one or more package materials used to construct one or more packages, the system comprising: one or more memory storage areas; and one or more processors configured for executing the steps of: receiving package materials data pertaining to the sustainability of one or more package materials used to construct a package; storing the package materials data in at least one of the memory storage areas; and determining, based on the package materials data, whether the packages have satisfied a set of predefined sustainability criteria.

DETAILED DESCRIPTION OF VARIOUS
EMBODIMENTS OF THE INVENTION

Various embodiments of the present invention will now be described more fully with reference to the accompanying drawings, in which some, but not all embodiments of the invention are shown. Indeed, various embodiments of the invention may be embodied in many different forms and should not be construed as limited to the embodiments set forth herein. Like numbers refer to like elements throughout.

As will be appreciated by one skilled in the art, various embodiments of the present invention may be embodied as a method, a data processing system, or a computer program product. Accordingly, various embodiments of the present invention may take the form of an entirely hardware embodiment, an entirely software embodiment, or an embodiment combining software and hardware aspects. Furthermore, various embodiments of the present invention may take the form of a computer program product on a computer-readable storage medium having computer-readable program instructions (e.g., computer software) embodied in the storage medium. More particularly, various embodiments of the present invention may take the form of web-implemented computer software. Any suitable computer-readable storage medium may be utilized including hard disks, CD-ROMs, optical storage devices, or magnetic storage devices.

Various embodiments of the present invention are described below with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations for performing the specified functions, combinations of steps for performing the specified functions, and program instructions for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Overview

According to various embodiments of the present invention, a package evaluation system is provided for evaluating the sustainability of packaging used in the shipment of goods. The package evaluation system may be used, for example, by a shipping entity (e.g., United Parcel Service, Inc., FedEx Corp., United States Postal Service) in evaluating the sustainability of its customers' transport packaging systems and offering an environmental certification for those customers based on the evaluation. A shipping entity customer (herein "shipper") obtaining certification may then be authorized to ship packages with a graphic or logo indicating the shipper's certification. The certification process enabled by the package evaluation system allows shippers to optimize the sustainability of their shipping practices and convey their environmental awareness to package recipients.

According to various embodiments, the package evaluation system is configured to capture, store, manage, evaluate, and provide access to data associated with various packaging evaluations used in the certification process. For example, as part of the certification process, a shipper (e.g., a retailer, manufacturer, or other shipper of goods) may be required to submit for evaluation one or more sample packages, and/or sample package data, representative of the packaging used in its transport packaging system. The shipping entity, or a third party, may then conduct a series of package evaluations designed to assess various environmentally significant aspects of the sample packages. As will be discussed in greater detail below, each evaluation may comprise one or more specific tests. As a metric for obtaining certification, the shipping entity may specify certain criteria or standards for the various evaluations that must be satisfied by the sample packages in order for the shipper to receive certification of its transport packaging system. The package evaluation system may be used by the shipping entity during the certification process to receive and store package data used in various evaluations, perform certain evaluations, store records of testing data used as a basis for the certification (or non-certification), determine whether sample packaging has met the shipping entity's standards for certification, and identify aspects of the sample packaging that may be modified to improve the overall sustainability of the customer's transport packaging system.

According to various embodiments, the package evaluations facilitated by the package evaluation system are designed to assess, among other things, the ability of sample packages to prevent damage to their contents, the volumetric efficiency of sample packages, and the sustainability of the materials used to construct sample packages. In certain embodiments, each of these package aspects may be assessed by a separate evaluation comprised of one or more individual tests. FIG. 1 shows a block diagram of a transport packaging system certification process 900 comprised of three distinct package evaluations. The illustrated evaluations include a damage prevention evaluation 910, a volume efficiency evaluation 920, and a package materials evaluation 930. Each of these evaluations are directed toward package aspects that are typically controlled by the shipper and that may affect the sustainability and overall environmental impact of the shipper's transport packaging system.

For example, if an item shipped in a package is damaged during shipment, a subsequent replacement item will likely be shipped. This additional shipment will require additional fuel for transportation and additional materials for packaging. Accordingly, in the embodiment illustrated in FIG. 1, the damage prevention evaluation 910 comprises a shock test 911, a vibration test 912, and an atmospheric conditions test 913. As will be described in more detail below, the tests 911, 912, 913 generally assess the ability of one or more sample packages to protect their contents from various conditions (e.g., shock, vibration, atmospheric conditions).

In addition, packages that are larger than necessary use excessive packaging material and waste fuel by reducing the number of items that may be shipped within a given shipping vehicle. Accordingly, in the embodiment illustrated in FIG. 1, the volume efficiency evaluation 920 comprises a product-to-package volume test 921. Generally, the product-to-package volume test 921 assesses the volumetric efficiency of one or more sample packages by comparing the volume of the product shipped within a given package to the volume of the package itself Furthermore, the materials from which packages are constructed may have environmental significance in a number of ways. For example, packaging materials that are environmentally harmful to produce or incapable of being reused or recycled are less desirable from an environmental perspective than materials with more sustainable properties. Accordingly, in the embodiment illustrated in FIG. 1, the package materials evaluation 930 comprises a sustainable materials test 931. The sustainable materials test 931 generally assesses the overall sustainability of the materials used to construct one or more packages by accounting for various environmentally significant aspects of the materials used.

As will be appreciated by one of skill in the art, however, transport packaging system evaluations facilitated by the package evaluation system may comprise various other evaluations directed toward additional aspects of the sample packages. In addition, each evaluation may comprise fewer or additional tests for assessing the sustainable aspects of packages.

System Architecture

A package evaluation system 5 according to one embodiment is shown in FIG. 2. In the illustrated embodiment, the system 5 includes one or more evaluation computers 10, 12, 14, one or more shipper computers 16, and a shipping entity server 20. These components are connected via a network 15 (e.g., a LAN or the Internet). The package evaluation system 5 is configured for storing data to an accessible database 30 that may be stored on (or, alternatively, stored remotely from) the shipping entity server 20. In other embodiments, the package evaluation system 5 further includes a label printing apparatus and package printing apparatus.

FIG. 3 is a schematic diagram of the shipping entity server 20 according to various embodiments. The shipping entity server 20 includes a processor 60 that communicates with other elements within the shipping entity server 20 via a system interface or bus 61. Also included in the shipping entity server 20 is a display device/input device 64 for receiving and displaying data. This display device/input device 64 may be, for example, a keyboard or pointing device that is used in combination with a monitor. The shipping entity server 20 further includes memory 66, which preferably includes both read only memory (ROM) 65 and random access memory (RAM) 67. The server's ROM 65 is used to store a basic input/output system 26 (BIOS), containing the basic routines that help to transfer information between elements within the shipping entity server 20.

In addition, the shipping entity server 20 includes at least one storage device 63, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 63 is connected to the system bus 61 by an appropriate interface. The storage devices 63 and their associated computer-readable media provide nonvolatile storage for a shipping entity server. It is important to note that the computer-readable media described above could be replaced by any other type of computer-readable media known in the art. Such media include, for example, magnetic cassettes, flash memory cards, digital video disks, and Bernoulli cartridges.

A number of program modules may be stored by the various storage devices and within RAM 65. Such program modules include an operating system 80, a data acquisition module 200, a damage prevention module 300, a volume efficiency module 400, a package materials module 500, and a certification module 600. According to various embodiments, the data acquisition module 200, the damage prevention module 300, volume efficiency module 400, package materials module 500, and certification module 600 control certain aspects of the operation of the shipping entity server 20 with the assistance of the processor 60 and operating system 80. In general, the data acquisition module 200 is configured to receive and store pre-evaluation data relating to shippers and sample packaging submitted for evaluation, and to make that data accessible over the network 15 for use in the certification process 900. The damage prevention module 300 is configured to receive, manage, store, and evaluate data resulting from the damage prevention evaluations of sample packages. The volume efficiency module 400 is configured to receive, manage, store, and evaluate data resulting from the volume efficiency evaluations of sample packages. The package materials module 500 is configured to receive, manage, store, and evaluate data resulting from the packaging material evaluations of sample packages. The certification module 600 is configured to determine whether a shipper has met all required standards set by the shipping entity for the certification of the shipper's transport packaging system, and to store final evaluation and certification data associated with a shipper and its sample packages. Embodiments of these modules are described in more detail below In a particular embodiment, these program modules 200, 300, 400, 500, and 600 are executed by the shipping entity server 20 and are configured to generate graphical user interfaces accessible via the Internet or other communications network. In other embodiments, one or more of the modules 200, 300, 400, 500, and 600 may be stored locally on the evaluation computers 10, 12, 14 and executed by one or more processors of the computers 10, 12, 14. According to various embodiments, the modules 200, 300, 400, 500, and 600 may send data to, receive data from, and utilize data contained in, the database 30. In addition, the database 30 may comprise one or more separate, linked databases.

Also located within the shipping entity server 20 is a network interface 74, for interfacing and communicating with other elements of a computer network. It will be appreciated by one of ordinary skill in the art that one or more of the shipping entity server 20 components may be located geographically remotely from other shipping entity server 20 components. Furthermore, one or more of the components may be combined, and additional components performing functions described herein may be included in the shipping entity server 20.

FIG. 4 illustrates the working relationship between the above-mentioned database, modules, and computers according to one embodiment. In particular, the data acquisition module 200 sends data to and receives data from a shipper computer 16, and retrieves and stores data on the database 30. The damage prevention module 300 sends data to and receives data from a first evaluation computer 10, and retrieves and stores data on the database 30. The volume efficiency module 400 sends data to and receives data from a second evaluation computer 12, and retrieves and stores data on the database 30. The package materials module 500 sends data to and receives data from a third evaluation computer 14, and retrieves and stores data on the database 30. The certification module 600 retrieves and stores data on the database 30. In various embodiments, a single evaluation computer may send data to the damage prevention module 300, volume efficiency module 400, and the package materials module 500. Embodiments of each of these modules are discussed in more detail below.

Database

According to various embodiments, the database 30 is configured to store shipper information, data resulting from the evaluations of sample packages, and data pertaining to the certification status of shippers. According to various embodiments, the database 30 is configured such that the data contained in the database 30 may be created, modified, read, copied, or otherwise manipulated by the various modules 200, 300, 400, 500, 600 and computers 10, 12, 14, 16.

As noted above, the package evaluation system 5 may include various modules such as the data acquisition module 200, damage prevention module 300, volume efficiency module 400, package materials module 500, and certification module 600. The following paragraphs describe aspects of these modules.

Data Acquisition Module

According to various embodiments, the data acquisition module 200 is configured to receive shipper and package data, format the received data, and store the received data in the database 30. As will be described in more detail below, certain shipper and package data must be received by a shipping entity before conducting the evaluations 910, 920, 930 (herein "pre-evaluation data"). As such, the data acquisition module 200 is further configured to monitor received shipper and package data and generate an alert (e.g., an email or message communicated via a user interface) indicating the evaluations for which all required pre-evaluation data has been received.

Shipper data received and stored by the data acquisition module 200 may include, for example, the shipper's name and customer number. The received package data includes data pertaining to various aspects of the sample packages submitted by a shipper. For example, each submitted sample package has a particular box type and fill type and is configured to ship a particular type of product. The "box type" specifies the size and configuration of a sample package's primary external protective structure (e.g., medium size standard box, small thin box, large tubular container). The "fill type" specifies the configuration of the package's internal protective structure (e.g., cardboard dividers, air bubbles, foam peanuts, no fill). The combination of a particular box type, fill type, and product results in a number of unique "package configurations" for the packages used in a shipper's transport packaging system. Accordingly, the package data received and stored by the data acquisition module 200 may include, for example, a description of the items certain sample packages are designed to contain, the box type and fill type of sample packages, the dimensions of sample packages, the weight of the sample packages, and the materials used to construct the sample packages.

FIG. 5 illustrates steps executed by the data acquisition module 200 according to one embodiment. Beginning at step 202, the data acquisition module 200 receives shipper and package data. According to certain embodiments, the data acquisition module 200 is configured to receive data from the shipper computer 16, from one or more of the evaluation computers 10, 12, 14, and from other computers or devices configured for accessing the shipping entity server 20 (e.g., via the network 15).

For example, the package evaluation system 5 permits a shipper to directly transmit shipper and/or package data to the data acquisition module 200 via the network 15 (e.g., without the need for a package technician to manually enter the data). In one embodiment, the data acquisition module 200 is configured to communicate with the shipper computer 16 via a user interface (e.g., web-based user interface provided on a shipping entity website). In such an embodiment, the user interface provides instructions to the shipper pertaining to the certification process 900 and permits the shipper to submit shipper and package data. The user interface facilitates the transfer of shipper and package data by allowing a user to either complete one or more user input forms provided on the website or submit one or more completed user input forms as electronic documents (e.g., a .pdf or .doc file).

According to various embodiments, the user input forms include various data fields that are configured to inform a shipper of the pre-evaluation data needed before one or more of the evaluations 910, 920, 930 may be performed and to facilitate the transfer of that pre-evaluation data to the data acquisition module 200. For example, FIG. 6 shows an exemplary shipper information form 250. As illustrated, a completed shipper information form 250 provides the shipping entity with general shipper information, such as a customer number(s), annual shipment statistics, and information indicating whether the shipper's shipments include certain types of products. As will be described in more detail below in relation to step 206, this information is used by the data acquisition module 200 in creating or updating a shipper profile.

In addition, FIG. 7 shows a damage prevention package information form 252. As illustrated, a completed damage prevention package information form 252 provides the shipping entity with, among other things, data specifying the various box types used by a shipper and the products shipped within each box type. In various embodiments, the shipper will provide information for each box type used in its transport packaging system. In addition, the damage prevention package information form 252 provides various damage prevention thresholds for each product-package combination. As will be described in more detail below, the information submitted in the damage prevention package information form 252 is used by package technicians and the damage prevention module 300 in conducting the damage prevention evaluation 910.

In addition, FIG. 8 shows a product-package dimension information form 254. As illustrated, a completed product-package dimension information form 254 provides the shipping entity with, among other things, data specifying the dimensions of products and box types comprising product-package combinations used in a shipper's transport packaging system. In addition, the product-package dimension information form 254 provides fragility class and packing configuration information for those product-package combinations. As will be described in more detail below, the information submitted in the product-package dimension information form 254 is used by the volume efficiency module 400 in conducting the volume efficiency evaluation 920.

In addition, FIG. 9 shows a package material information form 256. As is illustrated, a completed package material information form 256 provides the shipping entity with, among other things, data specifying the materials comprising a given package configuration used in a shipper's transport packaging system. In one embodiment, a shipper may be required to submit a completed package materials form 256 for each package configuration submitted for evaluation, with each package materials form 256 specifying all materials used to construct a given package configuration. As will be described in more detail below, the information submitted in the package material information form 256 is used by the package materials module 500 in conducting the package materials evaluation 930.

In various embodiments, a shipper may also send shipper and/or package data to the shipping entity in the form of hard-copy documents (e.g., via standard mail) or an electronic document or electronic data (e.g., via email or file transfer protocol). In such instances, the package evaluation system 5 permits a package technician to manually enter the received shipper and/or package data into one of the evaluation computers 10, 12, 14 (or another computer or device capable of accessing the shipping entity server 20) with the data being received by the data acquisition module 200.

Returning to FIG. 5, the process continues to step 204, where the data acquisition module 200 stores the shipper and package information received in step 202 in the database 30. In storing the received data in the database 30, the data acquisition module 200 is configured to format the data into a format specified by the shipping entity. For example, data received via one of the user input forms 250, 252, 254, 256 will be received in the desired format as the shipping entity configures the user input forms to its own preferences. However, if the data is received, for example, in the form of an electronic document containing the pre-evaluation data in an undesired format, the data acquisition module 200 will automatically format the data into the format or arrangement specified by the shipping entity (e.g., using methods known in the art).

Next, in step 206, the data acquisition module 200 either generates a shipper certification profile based on the received data (e.g., if no prior certification profile exists for the shipper associated with the received data) or updates an existing shipper certification profile with the received data (e.g., if a certification profile has been previously created for the shipper associated with the received data). The shipper certification profile is comprised of select data associated with a shipper and the evaluations being conducted for that shipper's transport packaging system. Generally, the shipper certification profile presents, at different levels, a summary of the overall status of a shipper's certification, as well as the status of and certain results from the various package evaluations. According to various embodiments, the package evaluation system 5 provides visibility to the shipper certification profile for users of the package evaluation system 5 (e.g., via the aforementioned user interface).

FIG. 10A shows a shipper certification profile 260 generated by the data acquisition module 200. The shipper certification profile 260 is shown viewed at the certification level, which presents the status of each of the evaluations 910, 920, 930 for a particular shipper. In generating a new shipper profile, the data acquisition module 200 creates the matrix and data fields shown in FIG. 10A, and inserts relevant data received in step 202 into the appropriate fields (e.g., the "shipper name" and "primary shipper number").

As shown, the shipper certification profile 260 provides data fields for the status of the evaluations 910, 920, 930, as well as the overall certification status of the shipper. These fields may be updated as the certification process moves forward and results are obtained for each evaluation. For example, FIG. 10B shows an updated version of the shipper certification profile 260 shown in FIG. 10A. As illustrated, the shipper certification profile 260 indicates that the packages submitted for evaluation by the shipper "ABC Company," which is associated with the primary shipper number "867," have failed the damage prevention evaluation 910, passed the volume efficiency evaluation 920, and passed the package materials evaluation 930. In the illustrated embodiment, certification of a shipper's transport packaging system requires that a shipper's submitted packages pass all three of the evaluations 910, 920, 930. As such, the overall certification status of "ABC Company" is listed as "fail." In addition, the shipper certification profile 260 indicates the overall scores achieved by the submitted packages for the volume efficiency evaluation 920 and the package materials evaluation 930. As will be described in more detail below, other levels of the shipper certification profile 260 provide a summary of data pertaining to each individual evaluation (e.g., comments, test results, or individual package data).

Finally, in step 208, the data acquisition module 200 reviews the data that has been received and stored and determines, for each of the evaluations 910, 920, 930, whether all required pre-evaluation data has been received. The data acquisition module 200 then generates an alert indicating the evaluations for which all required pre-evaluation data has been received. For example, in one embodiment, the data acquisition module 200 generates and sends an email to the email account of a package technician associated with the certification of a particular shipper. The email indicates which evaluations are ready to be performed and which evaluations must be postponed until further pre-evaluation data is received. In other embodiments, the alert may be in the form of a text message to a cellular device or a message shown via a user interface on one of the evaluation computers 10, 12, 14. In one embodiment, the data acquisition module 200 is further configured to send an alert (e.g., an email) to the shipper indicating the necessary data not yet received and requesting that the shipper submit such data.

In addition to providing a shipper or other user with the ability to upload pre-evaluation data, the data acquisition module 200 may be further configured to provide the shipper with further instructions for participating in the certification process 900 and other information relating to the certification process (e.g., associated fees, rules, and legal information) via a user interface (e.g., a web-based user interface) or by other communication means (e.g., email).

Damage Prevention Module

According to various embodiments, the damage prevention module 300 is configured to retrieve pre-evaluation damage prevention data and receive and store damage prevention data resulting from the damage prevention evaluation 910 of a shipper's transport packaging system. As described above, the damage prevention evaluation 910 assesses the ability of various packages to protect their intended contents. The damage prevention module 300 facilitates the performance of the damage prevention evaluation 910 by providing necessary pre-evaluation data to package technicians performing the evaluation 910, as well as managing and storing the data resulting from the evaluation 910.

FIG. 11 shows steps executed by the damage prevention module 300 according to one embodiment of the present invention. Beginning at step 301, the damage prevention module 300 retrieves the pre-evaluation data necessary for the damage prevention evaluation 910 from the database 30. In one embodiment, the damage prevention module 300 is configured to perform this step in response to a user request (e.g., user input received from one of the evaluation computers 10, 12, 14). For example, as discussed above in regard to the data acquisition module 200 step 208, a package technician may receive a notification that all of the pre-evaluation data has been received for the damage prevention evaluation 910. When the package technician is prepared to begin the evaluation, the package technician may submit a request to view the pre-evaluation data via one of the evaluation computers 10, 12, 14.

The pre-evaluation damage prevention data may include, for example, one or more of the data provided in the fields of the damage prevention package information form 252 shown in FIG. 7. According to one embodiment of the certification process 900, a shipper is required to submit sample packages representing each "box type" utilized in its transport packaging system. As such, the pre-evaluation damage prevention data provided in the damage prevention package information form 252 details each product-package combination (i.e., a separate set of data for each combination of a box type and a product type intended for shipment in that box type). For each product-package combination, the pre-evaluation damage prevention data includes a description of damage level thresholds for the indicated product type. In addition, according to one embodiment of the certification process 900, the damage prevention evaluation 910 is performed twice for each box type—once with the heaviest package configuration for a given box type (e.g., the heaviest package having the given box type when fully loaded with its intended product and fill materials) and once with the most fragile configuration for a given box type (e.g., the package containing a product that is most susceptible to damage when loaded into the given box type with fill materials). For this purpose, as shown in FIG. 7, the pre-evaluation damage prevention data indicates the heaviest and most fragile configuration for each box type. For example, in such an embodiment, if a shipper's transport packaging system utilizes six different box types to ship the shipper's various products, a damage prevention evaluation 910 will be performed for 12 product-package combinations (assuming the heaviest and most fragile package configurations are not the same for any particular box type).

Next, at step 302, the damage prevention module 300 displays the retrieved pre-evaluation damage prevention data, providing visibility to the data for the one or more package technicians performing the damage prevention evaluation 910. In one embodiment, this step is accomplished by displaying the retrieved pre-evaluation damage prevention data on a monitor connected to one of the evaluation computers 10, 12, 14. After displaying the data in step 302, the damage prevention module 300 waits to receive any data resulting from the damage prevention evaluation.

As described briefly above, the damage prevention evaluation 910 performed for each product-package combination comprises a series of damage prevention tests. In certain embodiments, the damage prevention evaluation 910 is comprised of tests specified in an industry standard (e.g., ISTA, ASTM, TAPPI). For example, in one embodiment, the damage prevention evaluation 910 is performed in accordance with the 2008 International Safe Transit Association (ISTA) 3A standard, which specifies tests for evaluating a package's ability to protect its contents from atmospheric conditions, shock, and vibrations. Accordingly, as shown in FIG. 1, the damage prevention evaluation 910 includes a series of shock tests 911, vibration tests 912, and atmospheric conditions tests 913 defined in the ISTA 3A standard.

In certain embodiments, these tests are carried out by package technicians by manually manipulating sample packages submitted by a shipper with an intended product packed within the sample package. In one embodiment, the results of the damage prevention evaluation 910 for each product-package combination are reported by a package technician in a package laboratory report, which may generated from user-input to one or more of the evaluation computers 10, 12, 14. FIG. 12 shows a package laboratory report 270 for the damage prevention evaluation of a box type "A2—Medium Standard Box" and product type "42—Six Candles." As is illustrated, the package laboratory report 270 includes "Acceptance Criteria" for passing the damage prevention evaluation, "Observations" made by the package technician pertaining to the performance of the product-package combination during the evaluation, and "Recommendations" for improving the package type in order to better protect the product type. In addition, the package laboratory report 270 includes "Results" indicating whether the product-package combination has passed or failed the evaluation. Throughout the damage prevention evaluation 910, the package technician may create similar package laboratory reports for each product-package combination tested for a given shipper.

In one embodiment, the damage prevention characteristics of tubular packages may be evaluated based on threshold dimensional requirements (e.g., in addition to or in place of the tests described above). For example, FIG. 15B shows a table of threshold dimensional values for tubular packages.

Referring back to FIG. 11, at step 304 the damage prevention module 300 receives the package laboratory report or other data resulting from the damage prevention evaluation 910 (herein "damage prevention data"). The damage prevention data (e.g., the data shown in the package laboratory report 270) may be entered directly into one of the evaluation computers 10, 12, 14, or included in a document transmitted to the shipping entity server 20 via other communication means (e.g., e-mail, file transfer protocol). For example, in one embodiment, the damage prevention data is automatically transmitted from the computer or device on which it was generated, via the network 15, to the shipping entity server 20, where it is received by the damage prevention module 300.

Next, at step 306, the damage prevention module 300 stores the damage prevention data in the database 30. Doing so preserves a record of the data on which the damage prevention evaluation is based, thus allowing the shipping entity or, if provided access, the shipper to refer back to the damage prevention data in the future.

Next, at step 308, the damage prevention module 300 updates the shipper certification profile 260. FIG. 13 shows the updated shipper certification profile 260 as viewed at the damage prevention evaluation level. As is illustrated, at the damage prevention evaluation level, the shipper certification profile 260 indicates the status of the damage prevention evaluation (e.g., pass, fail, or pending) for each product-package combination and provides a link to the package laboratory report associated with each product-package combination. For example, in accordance with the package laboratory report 270 described above, the shipper certification profile 260 indicates that the "A2" box type containing product "42" failed its damage prevention evaluation and provides a link to the package laboratory report 270. In addition, the links to the package laboratory reports allow shippers to view the analysis of each submitted package configuration and identify how to improve their packaging.

In the illustrated embodiment, the certification process requires that all packages submitted for damage prevention evaluation receive a passing score for the shipper to receive certification of its transport packaging system. Accordingly, as the combination of the "A2" package type and product type "42" failed its damage prevention evaluation, the shipper certification profile 260 indicates that the overall "Evaluation Status" of the damage prevention evaluation 910 for shipper "867," the "ABC Company," is "fail." This is also indicated at the certification level view of the shipper certification profile 260 shown in FIG. 10B. In other embodiments, the passage by all packages of all tests is not required.

Finally, at step 310, the damage prevention module 300 reviews the damage prevention data stored in step 306 to determine if the damage prevention evaluation 910 is complete. For example, in embodiments where the certification process requires a damage prevention evaluation for the heaviest and most fragile package configurations associated with each box type, the damage prevention module 300 is configured to review the damage prevention data and determine whether a completed package laboratory report and damage prevention status has been stored for the heaviest and most fragile configurations of each box type used by a given shipper. In addition, the damage prevention module 300 is further configured to generate an alert upon determining that the damage prevention evaluation 910 has been completed. Similar to the alert generated by the data acquisition module 200 in step 208, the alert may be in the form of an email, text message, or user interface message.

Alternative Embodiments of the Damage Prevention Module

In addition to the embodiments described above, other embodiments of the damage prevention module are contemplated as described below. An alternative set of steps that may be executed by the damage prevention module are described below. The following steps detail the steps executed by the damage prevention module in receiving and assessing the results of damage prevention tests performed in accordance with ISTA standards.

In a first step, the damage prevention module initiates an atmospheric conditions test. In one embodiment, this step may be accomplished by communicating authorization to begin the test to the first evaluation computer 10, being used by a package lab technician. According to another embodiment, this first step may be accomplished by sending an instruction to an automated testing apparatus to start the test. In another embodiment, this step may be omitted and the process may begin at the second step described below.

In one embodiment, the atmospheric conditions test may be performed by a group of trained technicians. For example, a technician, either manually or with the aid of an apparatus, may place a sample package in a testing chamber exposing the package to controlled temperature and humidity conditions. After a certain period of time, the technicians may inspect the condition of the sample package and its contents and report their findings in a variety of ways. In one embodiment, the technicians may assign a numerical atmospheric conditions test score based on their observations of the sample package's performance. According to another embodiment, the technicians may simply assign a "pass" or "fail" score based on their observations. In yet another embodiment, the technicians may make detailed measurements of the sample package before and after testing. In this embodiment, the technicians may measure dimensional or humidity changes to the sample package resulting from the test. For example, the technicians may measure humidity changes by placing a humidity sensor inside the sample package and measuring the change in humidity inside the package or by weighing the sample package at the conclusion of the test and determining the amount of moisture absorbed by the package. In certain embodiments, the effect of atmospheric conditions on the sample package may be measured by conducting shock tests and vibration tests, such as drop-testing the sample package or placing the sample package on a vibration table, after the sample package has been conditioned by the atmospheric conditions test. Conducting the damage prevention tests in this order may allow technicians to observe the effect of atmospheric conditions on the structural integrity of the sample package and its ability to protect its contents.

According to another embodiment, the atmospheric conditions test may be performed automatically by an automated testing apparatus. For example, a robotic apparatus may be configured to place a sample package in the testing chamber and assess dimensional or humidity changes to the package resulting from the test. This may be accomplished, for example, by three-dimensional scanning and modeling software, humidity sensors, and weight scales. The robotic apparatus may then report its measurements directly, or may use programmed logic to report a numerical atmospheric conditions test score or pass/fail score based on the measurements. In certain embodiments, the robotic apparatus may also test the effect of atmospheric conditions on the sample package by conducting shock tests and vibration tests, such as drop-testing the sample package or placing the sample package on a vibration table, after the sample package has been conditioned by the atmospheric conditions test.

Next, the damage prevention module receives the results of the atmospheric conditions test. In one embodiment, the results obtained in the atmospheric conditions test may be transmitted to the damage prevention module from the first evaluation computer 10 via the network 15 and the shipping entity server 20. The first evaluation computer 10 may transmit the results automatically or in response to manual data entry by a technician. According to another embodiment, these results may be transmitted directly from an automated testing apparatus conducting the atmospheric conditions testing via the network 15 and shipping entity server 20. Upon receipt of the atmospheric conditions data, the damage prevention module stores the data in the database 30.

Next, the damage prevention module evaluates the results of the atmospheric conditions tests. According to various embodiments, the damage prevention module may be programmed to evaluate the results of the atmospheric conditions test in different ways depending on how the results are reported. For example, if the atmospheric conditions test results are reported as a "pass" or "fail" score, the damage prevention module may be configured to store that score without further evaluation. If the atmospheric conditions test results are reported as a single numerical score, the damage prevention module may be configured to store the numerical score without further evaluation or assign a "pass" or "fail" score to the atmospheric conditions test based on a pre-defined threshold score. For example, the shipping entity may specify that on a scoring scale of 1-5, scores of 3 and higher are passing. If the atmospheric conditions test results are reported as raw technical data, such as dimensional or humidity measurements, the damage prevention module may be configured to plug the measurements into one or more pre-defined equations or algorithms and return a numerical or pass/fail score for the atmospheric conditions test. For example, if the results of the atmospheric conditions test include humidity measurements from the interior of the sample package taken before and after the test, the damage prevention module may be plug both measurements into an equation to measure the percentage change in humidity. The damage prevention module may then compare the result of this calculation to a pre-defined standard and assign a numerical or pass/fail score accordingly. According to various embodiments, the damage prevention module is also configured to store its evaluation of the atmospheric conditions test results in the database 30.

Next, the damage prevention module initiates a shock test. In one embodiment, this step may be accomplished by communicating authorization to begin the test to the first evaluation computer 10 being used by a package lab technician. According to another embodiment, the damage prevention module sends an instruction to an automated testing apparatus to start the test.

Next, the damage prevention module receives the results of the shock test. In one embodiment, the shock test may be performed by a group of trained technicians. For example, a technician may drop the sample package onto a surface from a fixed height or drop other objects onto the sample package. The technician may accomplish this manually or with the aid of an apparatus. After a certain period of time, the technicians may inspect the condition of the sample package and its contents and report their findings in a variety of ways. In one embodiment, the technicians may assign a numerical shock test score based on their observations of the sample package's performance. According to another embodiment, the technicians may simply assign a "pass" or "fail" score based on their observations. In yet another embodiment, the technicians may make detailed measurements of the sample package before and after testing. For example, the technicians may measure dimensional changes to the sample package resulting from the test or measure the structural integrity of the sample package. Similar measurements may be made to the sample package's contents.

According to another embodiment, the shock test may be performed automatically by an automated testing apparatus. For example, a robotic apparatus may be configured to drop the sample package onto a surface from a fixed height or drop other objects onto the sample package and assess dimensional or structural integrity changes to the package resulting from the test. This may be accomplished, for example, by three-dimensional scanning and modeling software. The robotic apparatus may then report its measurements directly, or may use programmed logic to report a numerical shock test score or pass/fail score based on the measurements.

In various embodiments, the results obtained in the shock test may be transmitted to the damage prevention module from the first evaluation computer 10 via the network 15 and shipping entity server 20. The first evaluation computer 10 may transmit the results automatically or in response to manual data entry by a technician. According to another embodiment, these results may be transmitted directly from an automated testing apparatus conducting the shock testing via the network 15 and shipping entity server 20. Upon receipt of the shock test data, the damage prevention module stores the data in the database 30.

Next, the damage prevention module evaluates the results of the shock test. According to various embodiments, the damage prevention module may be programmed to evaluate the results of the shock test in different ways depending on how the results are reported. For example, if the shock test results are reported as a "pass" or "fail" score, the damage prevention module may be configured to store that score without further evaluation. If the shock test results are reported as a single numerical score, the damage prevention module may be configured to store the numerical score without further evaluation or assign a "pass" or "fail" score to the shock test based on a pre-defined threshold score. For example, the shipping entity may specify that on a scoring scale of 1-5, scores of 3 and higher are passing. If the shock test results are reported as raw technical data, such as dimensional measurements, the damage prevention module may be configured to plug the measurements into one or more pre-defined equations or algorithms and return a numerical or pass/fail score for the shock test. For example, if the results of the shock test include dimensional measurements of the sample package taken before and after the test, the damage prevention module may be plug both measurements into an equation to measure the percentage change of a certain dimension of the sample package. The damage prevention module may then compare the result of this calculation to a pre-defined standard and assign a numerical or pass/fail score accordingly. According to various embodiments, the damage prevention module is also configured to store its evaluation of the shock test results in the database 30.

Next, the damage prevention module initiates a vibration test. In one embodiment, this step may be accomplished by communicating authorization to begin the test to the first evaluation computer 10 being used by a package lab technician. According to another embodiment, the damage prevention module sends an instruction to an automated testing apparatus to start the test.

Next, the damage prevention module receives the results of the vibration test. In one embodiment, the vibration test may be performed by a group of trained technicians. For example, a technician may place a sample package on a vibration table for extended periods. After a certain period of time, the technicians may inspect the condition of the sample package and its contents and report their findings in a variety of ways. In another embodiment, the technicians may apply a compressive force to the sample package while it is on the vibration table. This may be accomplished, for example, by placing a weight on top of the package.

In one embodiment, the technicians may assign a numerical vibration test score based on their observations of the sample package's performance. According to another embodiment, the technicians may simply assign a "pass" or "fail" score based on their observations. In yet another embodiment, the technicians may make detailed measurements of the sample package before and after testing. For example, the technicians may measure dimensional changes to the closure means of the sample package resulting from the test or measure the structural integrity of the sample package. Similar measurements may be made to the sample package's contents.

According to another embodiment, the vibration test may be performed automatically by an automated testing apparatus. For example, a robotic apparatus may be configured to place a sample package on a vibration table for extended periods and assess dimensional or structural integrity changes to the package resulting from the test. This may be accomplished, for example, by three-dimensional scanning and modeling software. The robotic apparatus may then report its measurements directly, or may use programmed logic to report a numerical vibration test score or pass/fail score based on the measurements.

In one embodiment, the results obtained in the vibration test may be transmitted to the damage prevention module from the first evaluation computer 10 via the network 15 and shipping entity server 20. The first evaluation computer 10 may transmit the results automatically or in response to manual data entry by a technician. According to another embodiment, these results may be transmitted directly from an automated testing apparatus conducting the vibration testing via the network 15 and shipping entity server 20. Upon receipt of the vibration test data, the damage prevention module stores the data in the database 30.

Next, the damage prevention module evaluates the results of the vibration test. According to various embodiments, the damage prevention module may be programmed to evaluate the results of the vibration test in different ways depending on how the results are reported. For example, if the vibration test results are reported as a "pass" or "fail" score, the damage prevention module may be configured to store that score without further evaluation. If the vibration test results are reported as a single numerical score, the damage prevention module may be configured to store the numerical score without further evaluation or assign a "pass" or "fail" score to the vibration test based on a pre-defined threshold score. For example, the shipping entity may specify that on a scoring scale of 1-5, scores of 3 and higher are passing. If the vibration test results are reported as raw technical data, such as dimensional or structural integrity measurements, the damage prevention module may be configured to plug the measurements into one or more pre-defined equations or algorithms and return a numerical or pass/fail score for the vibration test. For example, if the results of the vibration test include dimensional measurements of the sample package taken before and after the test, the damage prevention module may plug both measurements into an equation to measure the percentage change of a certain dimension of the sample package. The damage prevention module may then compare the result of this calculation to a pre-defined standard and assign a numerical or pass/fail score accordingly. According to various embodiments, the damage prevention module is also configured to store its evaluation of the vibration test results in the database 30.

Finally, the damage prevention module evaluates the atmospheric conditions test score, the shock test score, and the vibration test score to return an overall damage prevention evaluation. According to various embodiments, the damage prevention module may be programmed to evaluate the results of the various damage prevention tests in different ways depending on how the results are reported. For example, if each test score is reported as a "pass" or "fail" score, the damage prevention module may be configured to assign a pass/fail score to the damage prevention evaluation based on a pre-defined standard set by the shipping entity. For example, the shipping entity may specify that a sample package must pass all three damage prevention tests in order to achieve a passing damage prevention evaluation. If the damage prevention test scores are reported as a single numerical scores, the damage prevention module may be configured assign an overall "pass" or "fail" score to the damage prevention evaluation based on a pre-defined average threshold score. For example, the shipping entity may specify that on a scoring scale of 1-5, an average score for all damage prevention tests of 3 and higher is passing. The damage prevention module may also be configured to store the average of the damage prevention test scores without assigning an overall pass/fail score for the damage prevention evaluation. According to various embodiments, the damage prevention module is also configured to store its evaluation of the damage prevention test results in the database 30.

As would be recognized by one of ordinary skill in the art, the basic logic of the damage prevention module may be altered to fit the preferences of the shipping entity. In one embodiment, the shock test described above may be repeated after the completion of the atmospheric conditions test, a first shock test, and the vibration test. In other embodiments, the tests of the damage prevention evaluation may be completed in a different order. In further embodiments, the damage prevention evaluation may include only a subset of the tests described above. In additional embodiments, the damage prevention module may be configured to incorporate tests which differ from the exemplary damage prevention tests discussed above. In another embodiment, the damage prevention module may be configured to stop its evaluation if a sample package fails any particular damage prevention test. In yet another embodiment, the results of each damage prevention test included in the damage prevention evaluation may be weighted based on, for example, environmental importance. In other embodiments, the damage prevention module may be configured to evaluate the results of each damage prevention tests after all tests have been completed. In various other embodiments, the standard threshold scores and criteria used by the damage prevention module may be altered and defined by the shipping entity to meet the shipping entity's preferences for the evaluation. According to various embodiments, other criteria may be added to or substituted into the basic framework of the damage prevention module.

In various embodiments, the damage evaluations (e.g., atmospheric conditions, shock, and vibration evaluations) may be performed in sequence on each individual sample package. In other embodiments, each damage evaluation may be performed on a separate package sample.

Volume Efficiency Module

According to various embodiments, the volume efficiency module 400 is configured to retrieve pre-evaluation volume efficiency data, perform the volume efficiency evaluation 920 based on the retrieved data, and generate volume efficiency data indicating the volumetric efficiency of one or more sample packages. As described above, the volume efficiency evaluation 920 assesses the volumetric efficiency of various product-package combinations present in the transport packaging system of a shipper. In general, the volume efficiency module 400 performs this evaluation by calculating product-to-package volume ratios for each evaluated sample product-package combination and comparing the calculated ratios to a pre-defined threshold.

FIG. 14 shows steps executed by the volume efficiency module 400 according one embodiment. Beginning at step 402, the volume efficiency module 400 retrieves the pre-evaluation data necessary for the volume efficiency evaluation 920 from the database 30. In one embodiment, the volume efficiency module 400 is configured to perform this step in response to a user request (e.g., user input received from one of the evaluation computers 10, 12, 14). The pre-evaluation volume efficiency data may include, for example, the data provided in the fields of the product-package dimension information form 254, which specifies for each product-package combination the dimensions of the package type (e.g., length, width, and height), the dimensions of the product type (e.g., length, width, and height), fragility class of the product type (e.g., fragile, rugged, delicate), and the packing configuration of the product within the package (e.g., standard pack or pick and pack).

In the illustrated embodiment, the dimensions of the box type are representative of the internal volume of the package (i.e., the available space within a package a product may fit in). The dimensions of the product type are representative of the rectangular volume of the product. The rectangular volume is equivalent to the volume of the smallest right rectangular cuboid capable of enclosing the product. For example, the rectangular volume of a spherical object (e.g., a basketball) having a diameter of 10 inches would be equal to the be 1000 cubic inches (i.e., 10 in. (length)×10 in. (height)×10 in. (width)). As will be described in more detail below, in one embodiment, the volume of products shipped within tubular packages (e.g., posters) is not considered in the volume efficiency evaluation 920.

The fragility class indicated for each product in the product-package dimension information form 254 represents the level of fragility of each product type. In the illustrated embodiment, product types are classified as "Rugged," "Semi-Rugged," "Semi-Delicate," "Delicate," or "Fragile." Similarly, the packing configuration indicated for each product in the product-package dimension information form 254 represents the manner in which each product is packed within its associated package. In the illustrated embodiment, the packing configuration of each product is represented as "standard pack" or "pick and pack." "Standard pack" indicates that the product is packaged as part of a standardized package of products (e.g., a case of soft drinks) having a recurring size and volume and, as such, is frequently shipped within a package type configured for shipping that particular product. As will be discussed in more detail below, products shipped with a standard pack configuration may be held to a higher volume efficiency standard, as the package type can be easily tailored to the product due the standardized size of the product's packaging and the recurring shipment of that product. "Pick and pack" indicates that the product is packaged individually, or with other products, in a package type configured for more general use (e.g., a single picture frame). Products shipped with the pick and pack configuration may be held to a lower volume efficiency standard as shippers cannot be expected to have specifically designed package types for all of their combinations of products, particularly those that are shipped intermittently in response to specific customer demand.

Next, at step 404, the volume efficiency module 400 calculates the product-to-package ratio for each (non-tubular) product-package combination provided in the pre-evaluation volume efficiency data. For example, in the embodiment described above in which the pre-evaluation volume efficiency data includes the dimensions of the box type and product type for each product-package combination, the volume efficiency module 400 automatically calculates the relevant volume of the product and the package, then divides the calculated volume of the product by the calculated volume of the package. As will be described in more detail below, in the illustrated embodiment, a product-to-package ratio may not calculated for product-package combinations in which the package is tubular. As will be appreciated by one of ordinary skill in the art, the volume efficiency module 400 may be configured to determine the product-to-package ratios of each product-package combination based on other data (e.g., data specifying volumes as opposed to dimensions) and data presented in varying units of measure (e.g., millimeters as opposed to inches).

Next, at step 406, the volume efficiency module 400 calculates the average product-to-package ratio for all of the product-package combinations represented in pre-evaluation volume efficiency data. In one embodiment, this is accomplished by summing all of the product-to-package ratios and dividing by the number of product-package combinations represented in the pre-evaluation volume efficiency data.

Next, at step 408, the volume efficiency module 400 calculates an overall average threshold score for the volume efficiency evaluation 920 based on the fragility classes and packing configurations of all product-package combinations. In one embodiment, this is accomplished by assigning an individual threshold score to each product-package combination. The volume efficiency module 400 accomplishes this by referencing a look-up table of threshold scores arranged by fragility class and packing configuration. FIG. 15A shows an example threshold score look-up table. The volume efficiency module then averages all of the individual threshold scores assigned to the product-package combinations. The result represents the overall average threshold score for the volume efficiency evaluation 920.

Next, at step 410, the volume efficiency module 400 compares the average product-to-package ratio calculated in step 406 to the overall average threshold score calculated in step 408. If the average product-to-package ratio meets or exceeds the average threshold score, the volume efficiency module 400 determines that the shipper's transport packaging system has passed the volume efficiency evaluation 920. If the average product-to-package ratio is less than the average threshold score, the volume efficiency module 400 determines that the shipper's transport packaging system has failed the volume efficiency evaluation 920.

Next, at step 412, the volume efficiency module 400 stores the volume efficiency data (e.g., the calculated volumes, product-to-package ratios, and pass/fail determination) in the database 30. As described above in relation to the damage prevention module 300, storing the volume efficiency data preserves a record of all data on which the damage prevention evaluation is based, thus allowing the shipping entity or, if provided access, the shipper to refer back to the volume efficiency data in the future.

Next, at step 414, the volume efficiency module 400 updates the shipper certification profile 260. FIG. 16 shows an updated shipper certification profile 260 as viewed at the volume efficiency level. As illustrated, at the volume efficiency level, the shipper certification profile 260 indicates the overall status of the volume efficiency evaluation (e.g., pass, fail, or pending), the calculated average product-to-package ratio, the overall average threshold product-to-package ratio, and data pertaining to each of the product-package combinations (e.g., the calculated product-package ratio for each combination). Finally, at step 416, the volume efficiency module 400 notifies the shipping entity that the volume efficiency evaluation 920 has been completed (e.g., by generating an alert). For example, in certain embodiments, the volume efficiency module 400 generates an alert in the form of an email, text message, or user interface message.

Alternative Embodiments of the Volume Efficiency Module

In addition to the embodiments described above, an alternative embodiment of the volume efficiency module 400 is contemplated as described below.

According to certain embodiments, the volume efficiency module is configured to receive and assess data resulting from the volume efficiency evaluation of a sample package. In one embodiment, the volume efficiency evaluation may include a product-to-package volume test. The product-to-package volume test may be based on a calculation of the sample package's product-to-package volume ratio, which represents the quotient of the volume of a product being shipped divided by the volume of a sample package used to ship the product. In conjunction with the damage prevention evaluation, this ratio may be used to evaluate the volumetric efficiency of a sample package. From an environmental standpoint, packages having a high product-to-package volume ratio are preferred as long as they have acceptable damage prevention evaluations. Accordingly, the volume efficiency module is configured to receive data pertaining to the product-to-package volume ratio of a sample package and evaluate the data in terms of the sample package's damage prevention evaluation.

First, the volume efficiency module initiates a product-to-package volume test. In one embodiment, this step may be accomplished by communicating authorization to begin the test to the second evaluation computer 20, which may be used by a package lab technician. According to another embodiment, the first step may be accomplished by sending an instruction to an automated testing apparatus to start the test. In one embodiment, the product-to-package volume test may be performed manually by trained technicians. For example, a technician may take volumetric measurements of the sample package and its contents. The volume measurement of the product may represent the volume of the physical space occupied by the product within the sample package. For example, the relevant volume of a one liter pitcher would be equivalent to the sum of the displacement of the pitcher itself and the volume of its liquid-holding cavity. The relevant volume of a sample package may be its interior or exterior volume depending on the preferences of the shipping entity. In one embodiment, the technician may report the results of the product-to-package volume test as raw measurements. In another embodiment, the technician may calculate the product-to-package volume ratio and report the ratio, a numerical score, or pass/fail score based on the calculation.

According to another embodiment, the product-to-package volume test may be performed automatically by an automated testing apparatus. For example, a robotic apparatus may be configured to make dimensional measurements of the sample package and its contents. This may be accomplished, for example, by three-dimensional scanning and modeling software. The robotic apparatus may then report its measurements directly to the volume efficiency module. In another embodiment, the apparatus may calculate the product-to-package volume ratio and report the ratio, a numerical score, or pass/fail score based on the calculation. In yet another embodiment, the shipper providing the sample package may provide the necessary data (e.g., drawings, solid models, volumetric calculations) representing the relevant volumetric measurements.

Next, the volume efficiency module receives the results of the product-to-package volume test. In one embodiment, the results obtained in the product-to-package volume test may be transmitted to the volume efficiency module from a first evaluation computer 10 via the network 15 and shipping entity server 20. According to another embodiment, these results may be transmitted directly from an automated testing apparatus conducting the product-to-package volume testing via the network 15 and shipping entity server 20. Upon receipt of the product-to-package volume test data, the volume efficiency module stores the data in the database 30.

Next, the volume efficiency module evaluates the results of the product-to-package volume test. According to various embodiments, the volume efficiency module may be configured to evaluate the results of the product-to-package volume test in different ways depending on how the results are reported. In one embodiment, the results of the product-to-package volume test may be a pass/fail score assigned to the sample package by a technician or apparatus. In this embodiment, the volume efficiency module may be configured to store the result without further evaluation. In another embodiment, the results of the product-to-package volume test may be a numerical score assigned to the sample package by the technician or apparatus. In this embodiment, the volume efficiency module may be configured to either store the result without further evaluation or assign a pass/fail score for the product-to-package volume test based on a threshold score defined by the shipping entity. For example, the shipping entity may specify that for scores scaled 1-5, scores of 3 and higher are passing.

In yet another embodiment, the results of the product-to-package volume test may be raw data representing volumetric measurements of the sample package and its contents. In this embodiment, the volume efficiency module may be configured to evaluate the measurements in terms of the sample package's product-to-package volume ratio and the results of the sample package's damage prevention evaluation. For example, the shipping entity may specify a sample package receiving a passing volume efficiency score must either: (1) achieve a minimum product-to-package volume ratio and pass its damage prevention evaluation, or (2) show that its product-to-package volume ratio may not be reasonably reduced without failing the damage prevention evaluation.

To make this determination, the volume efficiency module may be configured to calculate the product-to-package volume ratio of the sample package in accordance with the equation below:

$$\text{Product to Package Volume Ratio} = \left(\frac{\text{Volume of Product}}{\text{Volume of Sample Package}}\right)$$

According to another embodiment, the product-to-package volume ratio may be calculated by a package lab technician or automated testing apparatus. In this embodiment, the volume efficiency module would receive the product-to-package volume ratio directly. The volume efficiency module may be configured to compare the calculated product-to-package volume ratio to the standard ratio set by the shipping entity and to determine if the sample package has passed its damage prevention evaluation by checking the data stored for the sample package in the database 30. If the volume efficiency module determines that both criteria are satisfied, it may return a "pass" score for the product-to-package volume test.

In another embodiment, the volume efficiency module may be configured to return a numerical score based on the difference between the sample package's product-to-package volume ratio and the standard ratio specified by the shipping entity. For example, the volume efficiency module may be configured to return a score of 5 if the sample package's product-to-package volume ratio is 10% or more greater than the standard ratio, 4 if it is 5% greater, 3 if it substantially meets the standard ratio, 2 if it is no more than 10% less than the standard ratio, 1 if it is no more than 20% less than the standard ratio, and 0 if it is more than 20% less than the standard ratio.

If the sample package's product-to-package volume ratio is less than the standard, the volume efficiency module must determine whether the sample package's product-to-package volume ratio may be reasonably reduced without failing the damage prevention evaluation. The volume efficiency module may make this determination in a variety of ways. In one embodiment, the volume efficiency module may request that the shipper submit a sample package of slightly reduced volume to be evaluated for its damage prevention capabilities. In another embodiment, the volume efficiency module may receive such a determination by trained technicians by way of an indication sent from the second evaluation computer 12 via the network 15 and shipping entity server 20. In yet another embodiment, the volume efficiency module may compare the sample package's damage prevention scores, stored in the database 30, to the scores required to pass the damage prevention evaluation. If the sample package passed the damage prevention evaluation by a score margin equal to or less than a predetermined threshold, the volume efficiency module may determine that reducing the product-to-package volume ratio will likely cause the sample package to fail the damage prevention test. In yet another embodiment, the shipping entity may specify a numerical index applied to all sample packages based on the fragility of the sample package's contents. In this embodiment, the volume efficiency module may be configured to adjust the minimum required product-to-package volume ratio based on the sample package's fragility index.

Finally, the volume efficiency module evaluates the volume efficiency test scores to return an overall volume efficiency evaluation. In one embodiment, the product-to-package volume test is the only volume efficiency test. Accordingly, the volume efficiency module may be configured to report the product-to-package volume test score as the overall volume efficiency score. However, according to other embodiments, the volume efficiency evaluation comprises additional tests. In these embodiments, the volume efficiency module may be programmed to evaluate the results of the volume efficiency tests in different ways depending on how the results are reported. For example, if each test score is reported as a "pass" or "fail" score, the volume efficiency module may be configured to assign a pass/fail score to the volume efficiency evaluation based on a pre-defined standard set by the shipping entity. For example, the shipping entity may specify that a sample package must pass all volume efficiency tests in order to achieve a passing volume efficiency evaluation. If the volume efficiency test scores are reported as a single numerical scores, the volume efficiency module may be configured to assign an overall "pass" or "fail" score to the volume efficiency evaluation based on a pre-defined average threshold score. For example, the shipping entity may specify that on a scoring scale of 1-5, an average score for all volume efficiency tests of 3 and higher is passing. The volume efficiency module may also be configured to store the average of the volume efficiency test scores without assigning an overall pass/fail score for the volume efficiency evaluation. According to various embodiments, the volume efficiency module is also configured to store its evaluation of the volume efficiency test results in the database 30.

As would be recognized by one of ordinary skill in the art, the basic logic of the volume efficiency module may be altered to fit the preferences of the shipping entity. In certain embodiments, the volume efficiency module may be configured to incorporate additional tests which differ from the product-to-package volume test described above. In one embodiment, the volume efficiency module may be configured to stop its evaluation if a sample package fails any particular volume efficiency test. In yet another embodiment, the results of each volume efficiency test included in the volume efficiency evaluation may be weighted based on, for example, environmental importance. In various other embodiments, the standard threshold scores and criteria used by the volume efficiency module may be altered and defined by the shipping entity to meet the shipping entity's preferences for the evaluation. According to various embodiments, other criteria may be added to or substituted into the basic framework of the volume efficiency module.

Package Materials Module

According to various embodiments, the package materials module 500 is configured to perform the package materials evaluation 930 based on a variety of pre-evaluation package materials data. As described above, the package materials evaluation 930 assesses the sustainability of the materials used to construct various package configurations utilized in a shipper's transport packaging system. In general, the package materials module 500 performs the package materials evaluation 930 by calculating, based on the pre-evaluation package materials data, an overall package materials score for each evaluated package configuration and comparing the calculated score to a predefined threshold score.

The package materials score calculated by the package materials module 500 is designed to provide a gauge of the overall sustainability of the materials used in a given package configuration. For example, if a given package configuration makes use of a certain material that requires a relatively low amount of fossil fuels to manufacture, that aspect of the package configuration will serve to increase the overall package materials score. However, if the same package configuration uses more of the certain material than is necessary (e.g., the walls of the package are unnecessarily dense), that aspect of the package configuration will serve to decrease the overall package materials score. As will be described in more detail below, by accounting for the various positive and negative sustainability traits of materials used to construct each evaluated package, the package materials score provides a metric by which to judge the sustainability of a wide variety of packages constructed from a wide variety of materials.

FIG. 17 shows steps executed by the package materials module 500 according to one embodiment. Beginning at step 502, the package materials module 500 selects a package configuration to evaluate. In one embodiment, the package materials module 500 is configured to perform this step in response to a user request (e.g., user input received from one of the evaluation computers 10, 12, 14) specifying a particular configuration of a particular box type. In another embodiment, the package materials module 500 automatically selects a package configuration to evaluate based on user-specified parameters. For example, a package evaluation system 5 user may specify that the package materials evaluation 930 shall be conducted for the heaviest configuration and most fragile configuration of each box type. In accordance with such parameters, the package materials module 500 will identify, for each box type used by the shipper, the heaviest configuration and the most fragile configuration based on pre-evaluation data submitted by the user (e.g., the damage prevention package information form 252). The package materials module 500 will then automatically select for evaluation one of the identified package configurations that have not yet been evaluated.

Next, in step 503, the package materials module 500 displays a package materials calculator user interface (e.g., via a monitor associated with the one of the evaluation computers 10, 12, 14). FIG. 18 shows an exemplary package materials calculator user interface 280 configured to allow a user to interact with the calculation functions of the package materials module 500. As illustrated, in calculating a package materials score for a selected package configuration, the package materials module 500 takes into account a variety of sustainability properties for each of the materials comprising the selected package configuration. For example, the user interface 280 divides materials into "shipping container" materials (e.g., the materials used to construct the box type of the selected package configuration) and "internal materials" (e.g., the materials positioned within the box type to provide additional product protection). The internal materials are further divided by their respective purpose (e.g., "fill," "divider," "wrap").

For each identified material, the user interface 280 provides a plurality of data fields corresponding to various physical attributes, efficiency attributes, and environmental impact attributes of each material. For example, physical attributes of the various materials may include measures of a material's weight (e.g., pounds per square foot), thickness (e.g., millimeters), and/or density (e.g., pounds per cubic foot). The efficiency attributes of each material may include whether the material was obtained from a source within 100 miles of its assembly point, whether the material is biodegradable in a composting facility or backyard environment, whether the material may be recycled widely or in a limited capacity, the number of times the material may be reused for its intended purpose, whether the material is comprised of a renewable resource, and the percentage of the material comprised of recycled content. The environmental impact attributes may include various relative measures of the fossil fuel consumption, greenhouse gas emissions, water consumption, biotic resource consumption, aquatic toxicity, mineral consumption, and eutrophication of each material. As will be described in more detail below, the environmental impact attributes may be accounted for in conjunction with one or more of the physical attributes a package configuration described above (e.g., the weight or thickness of the material).

Next, in step 504, the package materials module 500 automatically populates certain fields in the user interface 280 by retrieving pre-evaluation package materials data for the package configuration selected in step 502. In one embodiment, the package materials module 500 accomplishes this by first determining the materials comprising the selected package configuration from the pre-evaluation package materials data (e.g., based on data received in the package materials information form 256). The package materials module 500 then retrieves data corresponding to the appropriate data fields in the user interface 280 for each identified material from the database 30.

At least a portion of the data used to populate the user interface 280 is retrieved from the pre-evaluation package materials data received and stored by the data acquisition module 200. In particular, various values for the applicable physical attributes and efficiency attributes of each package material are retrieved from data storage. For example, the package materials information form 256 includes a field for indicating whether a particular material is sourced from a supplier within 100 miles of the package assembly point. If the shipper submits a complete package materials information form 256, this information would be accessibly stored in the database 30 by the data acquisition module 200 as part of the pre-evaluation package materials data. According to other embodiments, however, the fields of the package materials calculator 280 may also be populated manually by a package evaluation system 5 user via a computer (e.g., one of the evaluation computers 10, 12, 14).

Next, in step 505, the package materials module 500 calculates values for the environmental impact attributes. The values for the environmental impact attributes of the various package materials (e.g., shipping container materials, internal container/divider materials, internal wrap/film materials, internal cushion or fill materials) may be calculated based on the following general equation (herein "equation E1"):

$$\text{Attribute Value} = (\text{Relative Attribute Value}) \times \left(\frac{\text{Target Material Parameter}}{\text{Actual Material Parameter}}\right)$$

In regard to equation E1, the "relative attribute value" represents, with respect to a particular environmental impact attribute, the relative advantage of a particular material as compared to available alternative materials. In one embodiment, the relative attribute value for a given material and given environmental impact attribute is retrieved from a lookup table of relative attribute values stored on the database 30. For example, FIG. 19 shows a lookup table 285 of relative attribute values for the fossil fuel consumption of various internal cushion and fill materials. The relative attribute values in the table 285 represent, with respect to fossil fuel consumption, the relative advantage of each material as compared to alternative materials (with 1.0 being the most desirable material). For example, Quilted Kraft Paper (material ID "4") has a relative attribute value of "1.0" for fossil fuel consumption, indicating that—of all of the materials available for use as internal cushioning or fill—Quilted Kraft Paper uses the least amount of energy from fossil fuels in its manufacture. Likewise, a Low-Density Polyethylene (LDPE) Air Pillow has a score of "0.5," indicating that the manufacture of the LDPE Air Pillow consumes roughly 50% more energy from fossil fuels than Quilted Kraft Paper. These relative consumption values are provided as examples for illustrative purposes.

In certain embodiments, the package materials module 500 may be further configured to generate relative attribute value lookup tables (e.g., the lookup table 285) from other data. For example, in one embodiment, the package materials module 500 is configured to calculate the relative fossil fuel consumption values shown in the lookup table 285 from actual fossil fuel consumption data for each material (e.g., data specifying the megajoules of fossil fuel consumed for each material by weight). The actual fossil fuel consumption data may be derived from any suitable data source (e.g., the Sustainable Packaging Coalition's COMPASS online design software).

Referring back to the equation E1, the material parameter ratio (target material parameter/actual material parameter) serves to adjust the relative attribute value based on a particular parameter of each material. In certain embodiments, the material parameter ratio may represent a particular material parameter impacting the sustainability of a given material. For example, in one embodiment, the material parameter for materials constructed from paper is the basis weight of a given paper material (e.g., the "basis weight" attribute shown in FIG. 18). Accordingly, the material parameter ratio for paper materials (e.g., corrugated paper) would then be equivalent to a target basis weight (e.g., the "box strength baseline" shown in FIG. 18) divided by an actual basis weight for a given material (e.g., 80 pounds per thousand feet squared for shipping container material "cont. 1" in FIG. 18). In addition, the material parameter for plastic materials (e.g., a plastic container or plastic wrapping material) may be the thickness of a given plastic material (e.g., the "plastic thickness" attribute shown in FIG. 18). The material parameter ratio for plastic materials would then be equivalent to a target plastic thickness divided by an actual plastic thickness for a given material. In addition, the material parameter for foam wrap materials may be the thickness of a given foam wrap material (e.g., the "foam thickness" attribute shown in FIG. 18). The material parameter ratio for foam wrap materials would then be equivalent to a target foam thickness divided by an actual foam thickness for a given material. In addition, the material parameter for substantially solid foam materials (e.g., Styrofoam) may be the density of a given solid foam material (e.g., the "foam density" attribute shown in FIG. 18). The material parameter ratio for solid foam materials would then be equivalent to a target foam density divided by an actual foam density for a given material.

In one embodiment, the user interface 280 includes fields that allow a user to manually input the various target and actual material parameters. In another embodiment, the user interface 280 is configured to automatically determine the target and actual material parameters based on user input and/or stored data. For example, the user interface 280 includes a "shipping container strength" section that allows a user to input the weight of a package configuration and automatically retrieves a target basis weight from a lookup table based on the input package weight. In another embodiment, the package materials module 500 automatically retrieves the package weight from the pre-evaluation package materials data. In addition, in one embodiment, the package materials module 500 retrieves actual material parameters and target material parameters for each material from the pre-evaluation package materials data and/or other data stored on the database 30.

In general, equation E1 is configured to reflect the general concept that the level of sustainability indicated by the relative attribute value may be diminished if the package configuration uses a relatively large amount of the material or enhanced if the package configuration uses a relatively low amount of the material.

Next, at step 506, the package materials module 500 calculates an overall package materials score for the package configuration selected in step 502. To calculate the overall package materials score, the package materials module 500 first calculates a "total" score for each identified package material. In one embodiment, the total score for each material is calculated by summing the values of the efficiency attributes (where one point is awarded for each "yes" indication, no points are awarded for each "no indication, and one point is awarded for each indicated reuse) and the relative attribute values for each environmental impact attribute. For example, in FIG. 18, the data for material "Fill 1" indicates five "yes" answers for the efficiency attributes (totaling 5 points), one indicated reuse (totaling 1 point), and a relative attribute values for the environmental impact attributes totaling 1.2 points. When added together, material "Fill 1" has a total of 7.2 points (as indicated in the "total" column of FIG. 18). It should be understood that the fill material may be evaluated using equation E1.

Next, the package materials module 500 calculates an "adjusted total" score for each package material. This is accomplished by multiplying each material's total score by the percentage of the package's weight (for either the shipping container materials or internal materials) attributable to the material. For example, in FIG. 18, the only shipping container material is material "cont. 1." Accordingly, material "cont. 1" accounts for 100% of the weight of the shipping container materials and its total score is unadjusted. However, material "fill 1" accounts for 60% of the total weight of the package configuration's internal materials. Accordingly, "adjusted total" score for material fill 1 is 4.3 (i.e., 60% of 7.2).

Next, the package materials module 500 determines a "shipping container score" and "internal materials score" by summing the adjusted total scores of all materials in each class. As shown in FIG. 18, the shipping container score for the selected package configuration is 10.3, while the internal materials score is 7.6. Finally, the package materials module determines the "overall package materials score" by averaging the shipping container score and the internal materials score. As such, the overall package materials score for the selected package configuration in FIG. 18 is 9.0.

Next, in step 508, the package materials module 500 compares the calculated overall package materials score for the selected package configuration to a predefined package materials threshold score. For example, in one embodiment, a package evaluation system 5 user may specify the package materials threshold score as 9.0, with package configurations having score greater than or equal to the threshold satisfying the package materials criteria. Accordingly, the package materials module 500 will assign a package configuration satisfying the threshold a "pass" score and a package configuration not satisfying the threshold a "fail" score.

Next, at step 510, the package materials module 500 stores all of the package materials data generated as part of the package materials score calculation in the database 30. This serves to preserve the data as a record of the individual package materials evaluation of the selected package configuration.

Next, at step 512, the package materials module 500 updates the shipper certification profile 260 with the results of the individual package materials evaluation of the selected package configuration. For example, FIG. 20 shows an updated version of the shipper certification profile viewed at the package materials evaluation level. As shown, the shipper certification profile 260 indicates the shipping container score, internal materials score, and overall package materials score for each package configuration. In the illustrated embodiment, the package materials module 500 is further configured to assign an overall pass or fail score for the package materials evaluation 930 of a shipper by reviewing the scores to each of a shipper's evaluated package configurations. In one embodiment, a package evaluation system 5 user may specify that all evaluated package configurations must receive a passing score in order for the shipper to pass the package materials evaluation 930. According to other embodiments, the criteria may be altered to require on a certain number of package configurations to pass, or to average the overall package materials scores of all evaluated package configurations and compare the average score to a certain threshold.

Next, at step 514, the package materials module 500 determines whether an overall package materials score has been calculated for all of the sample packages intended to be submitted by a shipper. If all package configurations have not been tested, the package materials module 500 moves back to step 502 to select another package configuration for evaluation and repeats steps 502-514. If all package configurations have been tested, the package materials module 500 generates a notification (e.g., email, text message, message via user interface) to the shipping entity that the package materials evaluation 930 is completed.

Alternative Embodiments of the Package Materials Module

In addition to the embodiments described above, an alternative embodiment of the package materials module 500 is contemplated as described below.

According to certain embodiments, the package materials module is configured to receive and assess data resulting from an evaluation of the packaging materials used to construct a sample package. The package materials evaluation may be conducted based on a variety of test criteria relating to the materials used in the packaging. According to certain embodiments, the package materials evaluation may consider the recycled content of packaging materials, the amount of packaging material used, the reusability and recyclability of packaging materials, the recovery value of packaging materials, and the up-cycling potential of packaging materials. In one embodiment, one or all of these test criteria may be evaluated individually and the sample package may be assigned a numerical score for each criteria. An average of the numerical scores for all test criteria may represent an overall score for the sample package's package materials evaluation. In another embodiment, the sample package may be assigned a "pass" or "fail" score for each test criteria, with a majority of passing scores required to pass the package materials evaluation.

The package materials module may initiate a recycled content test and receive recycled content data from the shipper. In one embodiment, this step may be accomplished by communicating authorization to enter data to the shipper computer 16. Once initiated, the package materials module may receive data pertaining to the recycled content of a sample package from the shipper computer 16. In one embodiment, this data may be entered by a shipper into the shipper computer 16. In another embodiment, this data may be stored on a shipper database accessible by the shipper computer 16. The recycled content data is then stored in the database 30, which is accessible by the third evaluation computer 14. In one embodiment a package technician using the third evaluation computer 14 may receive the recycled content data stored on the database 30, and examine the sample package to confirm the presence of the claimed recycled content.

Next, the package materials module evaluates the recycled content data provided by the shipper. In one embodiment, the package materials module may be configured to calculate the percentage of recycled content of the sample package. This percentage may be expressed as a percentage by weight in accordance with the equation below.

$$\text{Percentage of Recycled Content} = \left(\frac{\text{Weight of Recycled Materials used in Sample Package}}{\text{Total Weight of Sample Package}}\right) \times 100$$

For example, if the walls of a sample package are constructed of recycled cardboard weighing 12 ounces, the remaining materials used to construct the package are not recyclable, and the total weight of the package is 15 ounces, then the percentage of recycled content would be 80%. In the context of the certification process, a high recycled content percentage may be favorable to a shipper. According to other embodiments, the recycled content of a sample package may be expressed as a percentage by volume, as opposed to weight.

Based on the calculated percentage of recycled content, the package materials module may assign a recycled content test score to the sample package. In one embodiment, this score may be assigned based on a defined scale. For example, percentages of recycled content greater than 80% may be assigned a score of 5, percentages between 79% and 60% assigned a score of 4, percentages between 59% and 40% a score of 3, percentages between 39% and 20% a score of 2, and percentages less than 20% a score of 1. As will be appreciated by one of skill in the art, this scale may be adjusted to allow for more or less demanding requirements. Upon determining a recycled content test score, the package materials module stores the score in the database 30. In one embodiment, the package materials module may also assign a "pass" or "fail" score for the recycled content test based on the calculated recycled content test score.

Next, the package materials module initiates a material efficiency test and receives material efficiency data from the shipper. In one embodiment, this step may be accomplished by communicating authorization to enter data to a shipper computer 16. Once initiated, the package materials module may receive data pertaining to the material efficiency of a sample package from the shipper computer 16. In one embodiment, this data may be entered by a shipper into the shipper computer 16. In another embodiment, this data may be stored on a shipper database accessible by the shipper computer 16 and transmitted to the package materials module. The material efficiency data is then stored in the database 30, which is accessible by the third evaluation computer 14. In one embodiment a package technician using the third evaluation computer 14 may receive the material efficiency data stored on the database 30, and examine the sample package to confirm the accuracy of the material efficiency data.

Next, the package materials module evaluates the material efficiency data provided by the shipper. In one embodiment, the package materials module may be configured to calculate the material efficiency ratio of the sample package. In one embodiment, this ratio may be expressed as a quotient in accordance with the equation below.

$$\text{Material Efficiency Ratio} = \left(\frac{\text{Interior Volume of Sample Package}}{\text{Volume of Packaging Materials Used to Construct Sample Package}}\right)$$

For example, if the total volume of packaging materials used to construct a sample package (e.g., cardboard, tape, ink, glue) is 50 cubic centimeters and the interior volume of the sample package is 200 cubic centimeters, the material efficiency ratio is 4 (or 4:1). In the context of the certification process, a high material efficiency ratio may be favorable to the shipper. In another embodiment, the material efficiency ratio may be expressed as a ratio of the interior volume of the sample package to the weight of the packaging materials used to construct the sample package.

Based on the calculated material efficiency ratio, the package materials module may assign a material efficiency test score to the sample package. In one embodiment, this score may be assigned based on a defined scale. For example, material efficiency ratios greater than 40 may be assigned a score of 5, ratios between 39 and 30 assigned a score of 4, ratios between 29 and 20 a score of 3, ratios between 19 and 10 a score of 2, and ratios less than 10 a score of 1. As will be appreciated by one of skill in the art, this scale may be adjusted to allow for more or less demanding requirements. Upon determining a material efficiency score, the package materials module stores the score in the database 30. In one embodiment, the package materials module may also assign a "pass" or "fail" score for the material efficiency test based on the calculated amount of packaging material score.

Next, the package materials module initiates a reusability and recyclability test and receives reusability and recyclability data from the shipper. In one embodiment, this step may be accomplished by communicating authorization to enter data to the shipper computer 16. Once initiated, the package materials module may receive data pertaining to the reusability and recyclability of a sample package from the shipper computer 16. In one embodiment, this data may be entered by a shipper into the shipper computer 16. In another embodiment, this data may be stored on a shipper database accessible by the shipper computer 16 and transmitted to the package materials module. The reusability and recyclability data is then stored in the database 30, which is accessible by a third evaluation computer 14. In one embodiment a package technician using the third evaluation computer 14 may receive the reusability and recyclability data stored on the database 30, and examine the sample package to confirm the presence of materials claimed to be reusable or recyclable.

Next, the package materials module evaluates the reusability and recyclability data provided by the shipper. In one embodiment, the package materials module may be configured to calculate the reusability ratio of the sample package. In one embodiment, this ratio may be expressed as a quotient in accordance with the equation below.

$$\text{Reusability Ratio} = \left( \frac{\text{Volume of Sample Package Materials That May Be Reused or Recycled}}{\text{Total Volume of Sample Package Materials Used to Construct Sample Package}} \right)$$

For example, if 40 cubic centimeters of the materials used to construct a sample package may be reused or recycled and the total volume of the materials used to construct a sample package is 50 cubic centimeters, the reusability ratio is 0.80. In the context of the certification process, a high reusability ratio is favorable to a shipper. In another embodiment, the reusability ratio may be expressed as a ratio of the weight of the sample package materials that may be reused or recycled to the total weight of the sample package.

Based on the calculated reusability ratio, the package materials module may assign a reusability and recyclability test score to the sample package. In one embodiment, this score may be assigned based on a defined scale. For example, reusability ratios greater than 0.8 may be assigned a score of 5, ratios between 0.7 and 0.6 assigned a score of 4, ratios between 0.5 and 0.4 a score of 3, ratios between 0.3 and 0.2 a score of 2, and ratios less than 0.2 a score of 1. As will be appreciated by one of skill in the art, this scale may be adjusted to allow for more or less demanding requirements. Upon determining a reusability and recyclability test score, the package materials module stores the score in the database 30. In one embodiment, the package materials module may also assign a "pass" or "fail" score for the reusability and recyclability test based on the calculated reusability and recyclability score.

Next, the package materials module initiates a recovery value test and receives recovery value data from the shipper. In one embodiment, this step may be accomplished by communicating authorization to enter data to the shipper computer 16. Once initiated, the package materials module may receive data pertaining to the recovery value of a sample package from the shipper computer 16. In one embodiment, this data may be entered by a shipper into the shipper computer 16. In another embodiment, this data may be stored on a shipper database accessible by the shipper computer 16. The recovery value data is then stored in the database 30, which is accessible by a third evaluation computer 14. In one embodiment a package technician using the third evaluation computer 14 may receive the recovery value data stored on the database 30, and investigate the validity of the recovery value data submitted by the shipper.

Next, the package materials module evaluates the recovery value data provided by the shipper. In one embodiment, the package materials module may be configured to calculate the recovery value of the sample package. As discussed above, the recovery value may be calculated as the total recovery value of the package, or as the recovery return rate of the valued materials. In one embodiment, the recovery value of a sample package may be amount of money guaranteed to be returned when the package is submitted for recycling. For example, if a sample package is constructed of 15 ounces of recyclable cardboard, which is guaranteed to return \$0.05/ounce if returned to a certain recycling station, the recovery value of the sample package is \$0.75. In the context of the certification process, a higher recovery value is favorable to the shipper.

In one embodiment, materials may only qualify as having a recovery value if that value is guaranteed in some way. For example, if a local recycling center offers a certain rate for recyclable cardboard, but that rate may be discontinued, changed, or eliminated at any time, the rate is not eligible to be considered in the recovery value analysis. In other embodiments, the recovery value of the sample package may not be fixed and guaranteed. In further embodiments, a standard rate may be applied to all shippers. In yet another embodiment, the recovery value may be evaluated in terms of the recovery rate of return of the materials used to construct the sample package, as opposed to the total recovery value of the sample package. In this embodiment, the amount of recyclable materials used to construct the sample package has no impact on the recovery value evaluation. For example, a 10 ounce package made of materials with a \$0.90/ounce rate of return would be more favorable to a shipper than a 500 ounce package made of materials with a \$0.80/ounce rate of return.

Based on the calculated recovery value, the package materials module may assign a recovery value test score to the sample package. In one embodiment, this score may be assigned based on a defined scale. For example, recovery values of \$5 and above may be assigned a score of 5, values between \$4 and \$3 assigned a score of 4, values between \$2 and \$1 a score of 3, values between \$1 and \$0.50 a score of 2, and values less than \$0.50 a score of 1. In another embodiment, a similar scale may be adopted using recovery value rates, as opposed to total recovery values. As will be appreciated by one of skill in the art, this scale may also be adjusted to allow for more or less demanding requirements. Upon determining a recovery value test score, the package materials module stores the score in the database 30. In one embodiment, the package materials module may also assign a "pass" or "fail" score for the recovery value test based on the calculated recovery value score.

Next, the package materials module initiates an up-cycling potential test and receives up-cycling potential data from the shipper. In one embodiment, this step may be accomplished by communicating authorization to enter data to the shipper computer 16. Once initiated, the package materials module may receive data pertaining to the up-cycling potential of a sample package from the shipper computer 16. In one embodiment, this data may be entered by a shipper into the shipper computer 16 and the data transmitted to the package materials module. In another embodiment, this data may be stored on a shipper database accessible by the shipper computer 16. The up-cycling potential data is then stored in the database 30, which is accessible by the third evaluation computer 14. In one embodiment a package technician using the third evaluation computer 14 may receive the up-cycling potential data stored on the database 30, and examine the sample package to confirm the presence of materials claimed to have up-cycling potential.

Next, the package materials module evaluates the up-cycling potential data provided by the shipper. In one embodiment, the package materials module may be configured to calculate the percentage of up-cyclable content of the sample package. In the context of the certification process, up-cyclable materials may be those that are recyclable to a higher, more-valuable use. For example, certain plastics are up-cycable for use in making fleece jackets. In one embodiment, the up-cyclable percentage may be expressed as a percentage by weight in accordance with the equation below.

$$\text{Percentage of Up-Cyclable Content} = \left( \frac{\text{Weight of Up-Cyclable Materials used in Sample Package}}{\text{Total Weight of Sample Package}} \right) \times 100$$

For example, if a sample package uses up-cyclable plastic weighing 12 ounces, the remaining the materials used to construct the package are not up-cyclable, and the total weight of the package is 15 ounces, then the percentage of up-cyclable content would be 80%. In the context of the certification process, a high up-cyclable content percentage is favorable to a shipper. According to another embodiment, the up-cyclable content of a sample package may be expressed as a percentage by volume, as opposed to weight.

Based on the calculated percentage of up-cyclable content, the package materials module may assign an up-cycling potential test score to the sample package. In one embodiment, this score may be assigned based on a defined scale. For example, percentages of up-cyclable content greater than 80% may be assigned a score of 5, percentages between 79% and 60% assigned a score of 4, percentages between 59% and 40% a score of 3, percentages between 39% and 20% a score of 2, and percentages below 20% a score of 1. As will be appreciated by one of skill in the art, this scale may be adjusted to allow for more or less demanding requirements. Upon determining an up-cycling potential test score, the package materials module stores the score in the database 30. In one embodiment, the package materials module may also assign a "pass" or "fail" score for the up-cycling potential test based on the calculated up-cycling potential test score.

Next, the package materials module initiates a resource efficiency test and receives resource efficiency data from the shipper. In one embodiment, this step may be accomplished by communicating authorization to enter data to the shipper computer 16. Once initiated, the package materials module may receive data pertaining to the resource efficiency of a sample package from the shipper computer 16. In certain embodiments, this resource efficiency data may include information relating to the amount of certain resources used to manufacture a sample package (e.g., biotic material, minerals, water), the amount of greenhouse gases emitted during the manufacturing process, and the overall toxicity of the resources used to manufacture the sample package. In one embodiment, this data may be entered by a shipper into the shipper computer 16 and the data transmitted to the package materials module. In another embodiment, this data may be stored on a shipper database accessible by the shipper computer 16. The resource efficiency data is then stored in the database 30, which is accessible by a third evaluation computer 14.

Next, the package materials module evaluates the resource efficiency data provided by the shipper. In one embodiment, the package materials module may be configured to receive a resource efficiency score from a calculator system provided by a third-party (e.g., Sustainable Packaging Coalition). In this embodiment, the third-party calculator may provide a resource efficiency score based on calculations using the resource efficiency data provided by the shipper. In another embodiment, the data provided by the shipper may be evaluated against thresholds and the results evaluated by the package materials module to arrive at a resource efficiency score. Based on the resource efficiency score yielded by the calculations described above, the package materials module may assign a scaled resource efficiency test score to the sample package. The scaled resource efficiency score may be assigned based on a defined scale used in the other package materials tests described above. For example, the package materials module may assign a scaled resource efficiency score between 1 and 5 based on the resource efficiency score returned by the third-party calculator.

Upon determining the scaled resource efficiency test score, the package materials module stores the score in the database 30. In one embodiment, the package materials module may also assign a "pass" or "fail" score for the up-cycling potential test based on the calculated up-cycling potential test score.

Next, the package materials module evaluates the scores of all of the package materials tests and returns an overall package materials score. In one embodiment, the package materials module may be configured to calculate the average of all scores for the various package materials tests. In addition, the package materials module may determine whether the calculated average test score meets or exceeds a defined minimum required score. If the calculated average test score is less than the minimum required score, the package evaluation module assigns a "fail" score for the package materials evaluation of the sample package. If the calculated average test score meets or exceeds the minimum required score, the package evaluation module assigns a "pass" score of the package materials evaluation of the sample package.

In another embodiment, the logic of the package materials module may be reconfigured such that one or all of the package materials test criteria are evaluated individually. For example, the package materials module may instead compare the recycled content test score to a minimum required recycled content test score. If the sample package's recycled content test score meets or exceeds the minimum required score, the package materials module would move to the third step. If, however, the sample package's recycled content test score was less than the minimum required score, the package materials module would end and record a failing score. In addition, according to yet another embodiment, each individual package materials test may be assigned a "pass" or "fail" score, instead of a numeric score. In various other embodiments, the package materials tests described above may be conducted in different orders.

In various other embodiments, the standard threshold scores and criteria used by the package materials module may be altered and defined by the shipping entity to meet the shipping entity's preferences for the evaluation. In additional embodiments, the package materials module may be configured to incorporate tests which differ from the exemplary damage prevention tests discussed above. In other embodiments, the package materials evaluation may not include all of the package materials test described above. According to various other embodiments, other criteria may be added to or substituted into the basic framework of the package materials module.

Certification Module

According to various embodiments, the certification module 600 is configured to complete the certification process 900 by receiving and assessing the results of the evaluations 910, 920, 930 and granting or denying certification to an shipper based on the results of the evaluations. FIG. 21 shows exemplary steps executed by the certification module 600 in completing the certification process 900.

Beginning at step 602, the certification module 600 retrieves the overall results of damage prevention evaluation 910, volume efficiency evaluation 920, and package materials evaluation 930 for a particular shipper. As described above, the various modules 300, 400, 500 are configured to assign an overall pass or fail score for each of the evaluations 910, 920, 930. As the data resulting from each of the evaluations is stored on the database 30 as the evaluations are completed, the results are easily accessible by the certification module 600 via the network 15.

Next, at step 604, the certification module 600 determines whether has satisfied the criteria for certification of its transport packaging system. The criteria for certification may be specified by a package evaluation system 5 user. For example, in one embodiment, the criteria for certification is specified as a passing score achieved for each of the evaluations 910, 920, 930. Accordingly, in this embodiment, the certification module 600 reviews the overall pass/fail scores from each evaluation to determine whether the shipper has satisfied the certification criteria. As will be appreciated by one of skill in the art, the criteria for certification may take on a variety of forms including, but not limited to, certain threshold scores for one or more of the evaluations. In addition, the criteria for certification may be effectively adjusted by altering the criteria for individual evaluations (e.g., requiring that the damage prevention evaluation be conducted for all product-package combinations as opposed to the heaviest and most fragile package configuration for each box type).

Next, in step 606, the certification module 600 updates the certification status of the shipper in the data associated with that shipper stored in the database. This step also includes updating the shipper certification profile 260 at the certification level (e.g., as shown in FIG. 10B).

Next, in step 608, the certification module 600 generates a certification evaluation summary providing a brief overview of the results of the certification process 900 conducted for the shipper and instructions to the shipper for moving forward with the shipping entity's sustainability certification program. For example, FIG. 22 shows an example certification evaluation summary 290 for the "ABC Company." As illustrated, the certification evaluation summary 290 indicates generally the products and box types tested in the various evaluations, the results of each of the evaluations 910, 920, 930, and brief comments on each result. In one embodiment, in the event the shipper fails the certification process 900, the certification evaluation report will instruct the shipper to review the results of each evaluation (e.g., via a web-based user interface) as an indication of how to further improve their packaging.

Finally, in step 610, the certification evaluation summary 290 is automatically sent to the shipper (e.g., by email, or other electronic communication means). In one embodiment, the certification evaluation summary may also be sent in hard-copy form as a letter. In addition, the certification evaluation summary 290 sent to the shipper may further include instructions to the shipper for utilizing its certification (e.g., executing a licensing agreement, payment of fees). In one embodiment, the certification evaluation summary 290 may also indicate that the shipper is authorized to ship packages with a certification logo and may request instructions from the shipper regarding the uses of the certification logo. For example, an e-mail may indicate that the shipper has the option of printing the certification logo on packages itself, requesting labels bearing the certification logo from the shipping entity, or requesting that the shipping entity print the certification logo on packages shipped by the shipper. The shipper may send instructions to the shipping entity directly from the shipper computer 16 to the database 30 via the network 15 and shipping entity server 20, by e-mail to the shipping entity, or via a letter sent by standard mail.

As will be appreciated by one of ordinary skill in the art, the exemplary steps of the certification module 600, shown in FIG. 21, may be altered to reflect varying certification requirements set by the shipping entity.

Use of Package Graphics

According to additional embodiments of the package evaluation system 5, the shipping entity server may further include a package graphics module configured to receive instructions from the shipper regarding use of the certification logo and execute the shipper's instructions accordingly. For example, the package graphics module may receive a shipper's instructions regarding use of the certification logo via e-mail or directly via the shipper computer 16. Based on the instructions received from the user, the package graphics module may then take various actions to facilitate the shipper's use of the certification logo.

For example, if the package graphics module determines that the shipper has requested to print logos itself, the package graphics module may send an e-mail to the shipper indicating authorization to use the certification logo and including instructions on how to acquire the logo. In one embodiment, the e-mail may include a file containing the logo image for use in printing, or a link to a website where the logo may be downloaded. If the package graphics module determines that the shipper has not requested to print logos itself, the package graphics module may trigger the shipment of labels or stickers to the shipper having the certification logo that may be affixed to packages. In addition, the package graphics module may interface directly with a label printing apparatus configured for generating custom labels. In one embodiment, the package graphics module may indicate a certain level of certification obtained by a shipper that may be indicated on the labels being generated. In another embodiment, the label printing apparatus is configured for printing certification logos on the shipper's packages before they are shipped by the shipping entity.

According to one embodiment, the certification logo placed on the packages of certified shippers may include a small design with writing indicating the certification of the shipper shipping the package. For example, FIG. 23 shows a certified package 8 shipped with standard package information 82 and a certification logo 84 in the form of a tree design with the words "Green Certified" printed next to it. As will be appreciated by one of skill in the art, the certification log 84 may take the form of any graphical design or phrase effectively conveying the shipper's certification. In another embodiment, the certification logo 84 may include an overall score achieved by the shipper. As described above, in one embodiment, the evaluation modules 300, 400, and 500 may return overall numerical scores which may then be averaged by the certification module 600. The final overall score by the certification module 600 may be displayed on packages 8 shipped by the shipper. In yet another embodiment, the certification logo 84 may include an indication of a shipper's level of certification. For example, the certification module 600 may assign certification levels of achievement to shippers (e.g., silver, gold, platinum). In one embodiment, these achievement levels may be assigned in accordance with the shipper's final overall score. This certification level may be printed as part of, or along with, the certification logo 84 on the shipper's packages 8. For example, the certification logo 84 may include a gold medal graphic for gold certification status, or may print the words "gold certified" next to the certification logo.

CONCLUSION

Many modifications and other embodiments of the invention will come to mind to one skilled in the art to which this invention pertains having the benefit of the teachings presented in the foregoing descriptions and the associated drawings. Accordingly, it is to be understood that the invention is not to be limited to the specific embodiments disclosed and that modifications and other embodiments are intended to be included within the scope of the invention. Although specific terms are employed herein, they are used in a generic and descriptive sense only and not for the purposes of limitation.

The invention claimed is:

1. A method for evaluating the sustainability of packaging used for shipping goods, said method comprising the steps of:
   receiving, via one or more processors, damage prevention data pertaining to the ability of a first set of one or more packages to prevent damage to a first set of one or more items;
   storing said damage prevention data in one or more memory storage areas;
   receiving, via said one or more processors, volume efficiency data, said volume efficiency data pertaining to the relative volume of a second set of one or more packages and a second set of one or more items;
   storing said volume efficiency data in at least one of said memory storage areas;
   receiving, via said one or more processors, package materials data pertaining to the sustainability of one or more package materials used to construct a third set of one or more packages;
   storing said package materials data in at least one of said memory storage areas; and
   determining, via said one or more processors, based on said damage prevention data, said volume efficiency data, and said package materials data, whether said first set of packages, said second set of packages, and said third set of packages have satisfied a set of predefined sustainability criteria.

2. The method of claim 1, further comprising the steps of:
   conducting a damage prevention evaluation of said first set of packages, said damage prevention evaluation assessing the ability of said first set of packages to prevent damage to said first set of items;
   generating, via one or more processors, said damage prevention data based, at least in part, on said damage prevention evaluation.

3. The method of claim 2, wherein:
   said first set of packages comprises a first package having a package configuration defining a first box type and a first fill type for containing one or more of a first item taken from the first set of items;
   said first set of packages further comprises a second package having a first package-type configuration for containing one or more of a second item from the first set of items;
   said step of conducting said damage prevention evaluation comprises the steps of:
      performing one or more damage prevention tests for each of said first set of packages, wherein:
         at least a portion of said damage prevention tests performed for said first package are performed with said first item positioned therein; and
         at least a portion of said damage prevention tests performed for said second package are performed with said second item positioned therein; and
      evaluating the damage prevention test performance of said first set of packages; and
   said step of generating said damage prevention data comprises the step of:
      inputting said damage prevention data to a computer, wherein said damage prevention data, at least in part, includes text describing said test performance of said first set of packages.

4. The method of claim 3, wherein:
   said first package comprises the heaviest package configuration for said first box type within the first set of packages; and
   said second package comprises the most fragile package configuration for said first box type within the first set of packages.

5. The method of claim 3, wherein:
   said step of conducting said damage prevention evaluation further comprises the step of:
      comparing said damage prevention test performance of said first set of packages to a predefined set of damage prevention criteria to determine whether the criteria is satisfied.

6. The method of claim 1, wherein:
   said second set of packages comprises a first package configured for containing one or more of the second-set items; and
   said received volume efficiency data comprises data indicating the ratio of the volume of said first package to the volume of said one or more second-set items.

7. The method of claim 6, wherein:
   said volume of said one or more second-set items is the theoretical volume of the smallest right rectangular cuboid capable of enclosing said one or more second-set items.

8. The method of claim 1, wherein:
   said second set of packages comprises a first package configured for containing one or more of the second-set items; and said method further includes the steps of:
calculating, based on said received volume efficiency data, a product-to-package ratio for said first package and said one or more items, wherein said product-to-package ratio is the ratio of a volume of said first package to a volume of said one or more second-set items; and
storing said calculated product-to-package ratio as volume efficiency data in at least one of said memory storage areas.

9. The method of claim 8, wherein:
said volume of said one or more second-set items is the theoretical volume of the smallest right rectangular cuboid capable of enclosing said first second-set item.

10. The method of claim 8, wherein said received volume efficiency data comprises data indicating dimensions of said first package and dimensions said first second-set item.

11. The method of claim 8, further comprising the step of determining whether said calculated product-to-package ratio satisfies a predefined set of volume efficiency criteria.

12. The method of claim 11, wherein said volume efficiency criteria comprises a threshold product-to-package ratio.

13. The method of claim 11, further comprising the step of associating said one or more second-set items with a degree of fragility; and
wherein said volume efficiency criteria is associated with said degree of fragility.

14. The method of claim 13, further comprising the step of associating said one or more second-set items with a type of packing configuration; and
wherein said volume efficiency criteria is further associated with said type of packaging configuration.

15. The method of claim 1, wherein said one or more package materials comprise one or more shipping container materials and one or more internal package materials.

16. The method of claim 15, wherein said internal package materials comprise one or more package materials selected from the group consisting of: cushion material, fill material, container material, divider material, wrap material, and film material.

17. The method of claim 15, wherein said package materials data comprise one or more physical attributes selected from the group consisting of: material type, weight, thickness, and density.

18. The method of claim 15, wherein said package materials data comprise one or more efficiency attributes selected form the group consisting of: source location distance, biodegradability, recyclability, reusability, recycled content, and renewability.

19. The method of claim 15, wherein said package materials data comprise one or more environmental impact attributes from the group consisting of: fossil fuel consumption, greenhouse gas emissions, water consumption, biotic resource consumption, aquatic toxicity, mineral consumption, and eutrophication.

20. The method of claim 1, further comprising the step of determining a package materials score based on said package materials data, said package materials score being indicative of the sustainability of said package materials.

21. The method of claim 1, wherein said set of predefined sustainability criteria comprises:
(i) said first set of packages satisfying a predefined set of damage prevention criteria;
(ii) said second set of packages satisfying a predefined set of volume efficiency criteria; and
(iii) said package materials used to construct said third set of packages satisfying a predefined set of package materials criteria.

22. The method of claim 1, further comprising the step of:
assigning a certification to a transport packaging system based on said determination, said transport packaging system utilizing said first set of packages, said second set of packages, and said third set of packages to ship, at least, said first set of items and said second set of items.

23. The method of claim 1, wherein:
said first set of packages, said second set of packages, and said third set of packages comprise the same package type.

24. A system for evaluating the sustainability of packaging used for shipping goods, said system comprising:
one or more memory storage areas; and
one or more processors configured for executing the steps of:
receiving damage prevention data pertaining to the ability of a first set of one or more packages to prevent damage to a first set of one or more items;
storing said damage prevention data in one or more memory storage areas;
receiving volume efficiency data, said volume efficiency data pertaining to the relative volume of a second set of one or more packages and a second set of one or more items;
storing said volume efficiency data in at least one of said memory storage areas;
receiving package materials data pertaining to the sustainability of one or more package materials used to construct a third set of one or more packages;
storing said package materials data in at least one of said memory storage areas; and
determining based on said damage prevention data, said volume efficiency data, and said package materials data, whether said first set of packages, said second set of packages, and said third set of packages have satisfied a set of predefined sustainability criteria.

25. The system of claim 24, wherein:
said damage prevention data comprises data resulting from a damage prevention evaluation of said first set of packages;
said processors are further configured for determining, based on said damage prevention data, whether said first set of packages have satisfied a predefined set of damage prevention criteria associated with said damage prevention evaluation.

26. The system of claim 24, wherein:
said second set of packages comprises a first package;
said second set of items comprises one or more first items, wherein said first package is configured for containing said first items; and
said received volume efficiency data comprises data indicating the ratio of the volume of said first package to the volume of said first items.

27. The system of claim 24, wherein:
said second set of packages comprises a first package;
said second set of items comprises one or more first items, wherein said first package is configured for containing said first items; and
said one or more processors are further configured for executing the steps of:
calculating, based on said volume efficiency data, a product-to-package ratio for said first package and said first items, wherein said product-to-package ratio is the ratio of said volume of said first package to said volume of said first items; and storing said calculated product-to-package ratio in at least one of said memory storage areas.

28. The system of claim 27, wherein:

said volume of said first items is the theoretical volume of the smallest right rectangular cuboid capable of enclosing said first items.

29. The system of claim 27, wherein said processors are further configured for determining whether said calculated product-to-package ratio satisfies a predefined set of volume efficiency criteria.

30. The system of claim 29, wherein said volume efficiency criteria comprises a threshold product-to-package ratio.

31. The system of claim 30, wherein said processors are further configured for:

associating said first items with a degree of fragility based on said volume efficiency data; and retrieving said volume efficiency criteria from at least one of said memory storage areas, wherein said volume efficiency criteria is associated with said degree of fragility.

32. The system of claim 31, wherein said processors are further configured for:

associating said first items with a type of packing configuration based on said volume efficiency data; and wherein said volume efficiency criteria is further associated with said type of packing configuration.

33. The system of claim 24, wherein said processors are further configured for determining a package materials score based on said package materials data, said package materials score being indicative of the sustainability of said package materials.

34. The system of claim 33, wherein said processors are further configured for determining whether said package materials score satisfies a predefined set of package materials criteria.

35. The system of claim 24, wherein said package materials comprise one or more shipping container materials and one or more internal package materials.

36. The system of claim 35, wherein said internal package materials comprise one or more materials selected from the group consisting of: cushion material, fill material, container material, divider material, wrap material, and film material.

37. The system of claim 24, wherein said package materials data comprise data pertaining to one or physical more attributes of said package materials selected from the group consisting of: material type, weight, thickness, and density.

38. The system of claim 24, wherein said package materials data comprise one or more efficiency attributes of said package materials selected form the group consisting of: source location distance, biodegradability, recyclability, reusability, recycled content, and renewability.

39. The system of claim 24, wherein said package materials data comprises one or more environmental impact attributes of said package materials selected from the group consisting of: fossil fuel consumption, greenhouse gas emissions, water consumption, biotic resource consumption, aquatic toxicity, mineral consumption, and eutrophication.

40. The system of claim 24, wherein said set of predefined sustainability criteria comprises:

(i) said first set of packages satisfying a predefined set of damage prevention criteria;

(ii) said second set of packages satisfying a predefined set of volume efficiency criteria; and (iii) said third set of packages satisfying a predefined set of package materials criteria.

41. The method of claim 24, wherein said processors are further configured for:

assigning a certification to a transport packaging system based on said determination.

\* \* \* \* \*